(12) United States Patent
Major et al.

(10) Patent No.: US 11,568,984 B2
(45) Date of Patent: Jan. 31, 2023

(54) SYSTEMS AND METHODS FOR DEVICE INVENTORY MANAGEMENT AND TRACKING

(71) Applicant: ZOLL MEDICAL CORPORATION, Chelmsford, MA (US)

(72) Inventors: David C. Major, Pittsburgh, PA (US); Wade T. Braden, Glenshaw, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 321 days.

(21) Appl. No.: 16/582,673

(22) Filed: Sep. 25, 2019

(65) Prior Publication Data
US 2020/0105404 A1    Apr. 2, 2020

Related U.S. Application Data

(60) Provisional application No. 62/738,262, filed on Sep. 28, 2018.

(51) Int. Cl.
*G16H 40/20* (2018.01)
*G16H 20/30* (2018.01)
*G06Q 10/08* (2012.01)

(52) U.S. Cl.
CPC ........... *G16H 40/20* (2018.01); *G06Q 10/087* (2013.01); *G16H 20/30* (2018.01)

(58) Field of Classification Search
CPC .................................................. G06Q 10/087
See application file for complete search history.

(56) References Cited

U.S. PATENT DOCUMENTS

| 3,534,727 A | 10/1970 | Roman |
| 3,553,651 A | 1/1971 | Bird et al. |

(Continued)

FOREIGN PATENT DOCUMENTS

| CN | 101031334 A | 9/2007 |
| CN | 101657229 A | 2/2010 |

(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/full/166/1/111.

(Continued)

*Primary Examiner* — Reginald R Reyes
(74) *Attorney, Agent, or Firm* — Lando & Anastasi, LLP

(57) ABSTRACT

An inventory management system includes a wearable cardiac device comprising an associated plurality of separate wearable cardiac device components stored as inventory at a first inventory location; a plurality of communication interface circuits associated with a corresponding one of the plurality of separate wearable cardiac device components and configured to facilitate transmission of inventory information through a network; at least one server device disposed at a central location and comprising a processor; and a memory comprising instructions that cause the processor to receive the inventory information from the plurality of communication interface circuits; receive a prescription for a patient; retrieve one or more prescription parameters based on the prescription; locate, in the inventory information, the wearable cardiac device based on the prescription parameters; determine a deployment status of the wearable cardiac device; and select the wearable cardiac device for the patient.

16 Claims, 18 Drawing Sheets

(56) References Cited

U.S. PATENT DOCUMENTS

| | | |
|---|---|---|
| 4,094,310 A | 6/1978 | McEachern et al. |
| 4,136,690 A | 1/1979 | Anderson et al. |
| 4,422,459 A | 12/1983 | Simson |
| 4,432,368 A | 2/1984 | Russek |
| 4,458,691 A | 7/1984 | Netravali |
| 4,632,122 A | 12/1986 | Johansson et al. |
| 4,698,848 A | 10/1987 | Buckley |
| 4,928,690 A | 5/1990 | Heilman et al. |
| 4,978,926 A | 12/1990 | Zerod et al. |
| 4,991,217 A | 2/1991 | Garrett et al. |
| 5,000,189 A | 3/1991 | Throne et al. |
| 5,062,834 A | 11/1991 | Gross et al. |
| 5,078,134 A | 1/1992 | Heilman et al. |
| 5,176,380 A | 1/1993 | Evans et al. |
| 5,243,978 A | 9/1993 | Duffin, Jr. |
| 5,330,505 A | 7/1994 | Cohen |
| 5,342,404 A | 8/1994 | Alt et al. |
| 5,348,008 A | 9/1994 | Bomn et al. |
| 5,353,793 A | 10/1994 | Bomn |
| 5,357,696 A | 10/1994 | Gray et al. |
| 5,365,932 A | 11/1994 | Greenhut |
| 5,381,798 A | 1/1995 | Burrows |
| 5,544,661 A | 8/1996 | Davis et al. |
| 5,564,429 A | 10/1996 | Bomn et al. |
| 5,652,570 A | 7/1997 | Lepkofker |
| 5,662,689 A | 9/1997 | Elsberry et al. |
| 5,716,380 A | 2/1998 | Yerkovich et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,827,196 A | 10/1998 | Yeo et al. |
| 5,887,978 A | 3/1999 | Lunghofer et al. |
| 5,924,979 A | 7/1999 | Swedlow et al. |
| 5,929,601 A | 7/1999 | Kaib et al. |
| 5,944,669 A | 8/1999 | Kaib |
| 6,016,445 A | 1/2000 | Baura |
| 6,045,503 A | 4/2000 | Grabner et al. |
| 6,047,203 A | 4/2000 | Sackner et al. |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen et al. |
| 6,169,387 B1 | 1/2001 | Kaib |
| 6,169,397 B1 | 1/2001 | Steinbach et al. |
| 6,221,010 B1 | 4/2001 | Lucas |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,405,082 B1 | 6/2002 | Borgenicht |
| 6,406,426 B1 | 6/2002 | Reuss et al. |
| 6,546,285 B1 | 4/2003 | Owen et al. |
| 6,602,191 B2 | 8/2003 | Quy |
| 6,609,023 B1 | 8/2003 | Fischell et al. |
| 6,666,830 B1 | 12/2003 | Lehrman et al. |
| 6,681,003 B2 | 1/2004 | Linder et al. |
| 6,690,969 B2 | 2/2004 | Bystrom et al. |
| 6,736,759 B1 | 5/2004 | Stubbs et al. |
| 6,790,178 B1 | 9/2004 | Mault et al. |
| 6,804,554 B2 | 10/2004 | Ujhelyi et al. |
| 6,827,695 B2 | 12/2004 | Palazzolo et al. |
| 6,865,413 B2 | 3/2005 | Halperin et al. |
| 6,893,395 B1 | 5/2005 | Kraus et al. |
| 6,908,437 B2 | 6/2005 | Bardy |
| 6,944,498 B2 | 9/2005 | Owen et al. |
| 6,961,612 B2 | 11/2005 | Elghazzawi et al. |
| 6,980,112 B2 | 12/2005 | Nee |
| 6,990,373 B2 | 1/2006 | Jayne et al. |
| 7,074,199 B2 | 7/2006 | Halperin et al. |
| 7,088,233 B2 | 8/2006 | Menard |
| 7,108,665 B2 | 9/2006 | Halperin et al. |
| 7,118,542 B2 | 10/2006 | Palazzolo et al. |
| 7,122,014 B2 | 10/2006 | Palazzolo et al. |
| 7,149,579 B1 | 12/2006 | Koh et al. |
| 7,177,684 B1 | 2/2007 | Kroll et al. |
| 7,220,235 B2 | 5/2007 | Geheb et al. |
| 7,277,752 B2 | 10/2007 | Matos |
| 7,295,871 B2 | 11/2007 | Halperin et al. |
| 7,307,509 B2 | 12/2007 | Chriss |
| 7,310,553 B2 | 12/2007 | Freeman |
| 7,340,296 B2 | 3/2008 | Stahmann et al. |
| 7,427,921 B2 | 9/2008 | Van Woudenberg |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,702,390 B1 | 4/2010 | Min |
| 7,712,373 B2 | 5/2010 | Nagle et al. |
| 7,794,384 B2 | 9/2010 | Sugiura et al. |
| 7,810,172 B2 | 10/2010 | Williams |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,290,574 B2 | 10/2012 | Feild et al. |
| 8,364,221 B2 | 1/2013 | Mannheimer et al. |
| 8,369,944 B2 | 2/2013 | Macho et al. |
| 8,428,704 B2 | 4/2013 | Johnson et al. |
| 8,600,486 B2 | 12/2013 | Kaib et al. |
| 8,644,925 B2 | 2/2014 | Volpe et al. |
| 8,649,861 B2 | 2/2014 | Donnelly et al. |
| 8,706,215 B2 | 4/2014 | Kaib et al. |
| 8,903,487 B1 | 12/2014 | Fischell et al. |
| 8,904,214 B2 | 12/2014 | Volpe et al. |
| 8,909,335 B2 | 12/2014 | Radzelovage |
| 8,983,597 B2 | 3/2015 | Whiting et al. |
| 9,007,216 B2 | 4/2015 | Oskin et al. |
| 9,008,801 B2 | 4/2015 | Kaib et al. |
| 9,060,683 B2 | 6/2015 | Tran |
| 9,135,398 B2 | 9/2015 | Kaib et al. |
| 9,283,399 B2 | 3/2016 | Donnelly et al. |
| 9,370,666 B2 | 6/2016 | Donnelly et al. |
| 9,398,859 B2 | 7/2016 | Volpe et al. |
| 9,579,516 B2 | 2/2017 | Kaib et al. |
| 9,597,523 B2 | 3/2017 | Kaib et al. |
| 9,676,313 B2 | 6/2017 | Morel et al. |
| 9,737,262 B2 | 8/2017 | Donnelly et al. |
| 9,737,701 B2 | 8/2017 | Dupelle et al. |
| 9,852,265 B1 * | 12/2017 | Treacy ............... G16H 10/60 |
| 9,878,171 B2 | 1/2018 | Kaib |
| 9,925,387 B2 | 3/2018 | Kaib et al. |
| 9,937,355 B2 | 4/2018 | Kaib et al. |
| 10,159,849 B2 | 12/2018 | Kaib et al. |
| 10,271,791 B2 | 4/2019 | Donnelly et al. |
| 10,485,982 B2 | 11/2019 | Kaib et al. |
| 10,582,858 B2 | 3/2020 | Volpe et al. |
| 2002/0107435 A1 | 8/2002 | Swetlik et al. |
| 2003/0004547 A1 | 1/2003 | Owen et al. |
| 2003/0023277 A1 | 1/2003 | Owen et al. |
| 2003/0032988 A1 | 2/2003 | Fincke |
| 2003/0055460 A1 | 3/2003 | Owen et al. |
| 2003/0095648 A1 | 5/2003 | Kaib et al. |
| 2003/0109904 A1 | 6/2003 | Silver et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2003/0233129 A1 | 12/2003 | Matos |
| 2004/0007970 A1 | 1/2004 | Ma et al. |
| 2004/0049233 A1 | 3/2004 | Edwards |
| 2004/0143297 A1 | 7/2004 | Ramsey |
| 2004/0162510 A1 | 8/2004 | Jayne et al. |
| 2004/0204743 A1 | 10/2004 | McGrath et al. |
| 2004/0249419 A1 | 12/2004 | Chapman et al. |
| 2005/0038345 A1 | 2/2005 | Gorgenberg et al. |
| 2005/0049515 A1 | 3/2005 | Misczynski et al. |
| 2005/0131465 A1 | 6/2005 | Freeman et al. |
| 2005/0144043 A1 | 6/2005 | Holland et al. |
| 2005/0177051 A1 | 8/2005 | Almen |
| 2005/0246199 A1 | 11/2005 | Futch |
| 2005/0261598 A1 | 11/2005 | Banet et al. |

(56) References Cited

U.S. PATENT DOCUMENTS

| | | |
|---|---|---|
| 2005/0283198 A1 | 12/2005 | Haubrich et al. |
| 2006/0017575 A1 | 1/2006 | McAdams |
| 2006/0036292 A1 | 2/2006 | Smith et al. |
| 2006/0079939 A1 | 4/2006 | Chen et al. |
| 2006/0085049 A1 | 4/2006 | Cory et al. |
| 2006/0095091 A1 | 5/2006 | Drew |
| 2006/0129067 A1 | 6/2006 | Grajales et al. |
| 2006/0136004 A1 | 6/2006 | Cowan et al. |
| 2006/0160522 A1 | 7/2006 | Jennings |
| 2006/0178706 A1 | 8/2006 | Lisogurski et al. |
| 2006/0189900 A1 | 8/2006 | Flaherty |
| 2006/0211934 A1 | 9/2006 | Hassonjee et al. |
| 2006/0220809 A1 | 10/2006 | Stigall et al. |
| 2006/0264776 A1 | 11/2006 | Stahmann et al. |
| 2006/0270952 A1 | 11/2006 | Freeman et al. |
| 2007/0073120 A1 | 3/2007 | Li et al. |
| 2007/0118056 A1 | 5/2007 | Wang et al. |
| 2007/0129769 A1 | 6/2007 | Bourget et al. |
| 2007/0143864 A1 | 6/2007 | Cabana et al. |
| 2007/0161913 A1 | 7/2007 | Farrell et al. |
| 2007/0169364 A1 | 7/2007 | Townsend et al. |
| 2007/0196320 A1 | 8/2007 | Yasin |
| 2007/0197878 A1 | 8/2007 | Shklarski |
| 2007/0239214 A1 | 10/2007 | Cinbis |
| 2007/0239220 A1 | 10/2007 | Greenhut et al. |
| 2007/0265671 A1 | 11/2007 | Roberts et al. |
| 2007/0299474 A1 | 12/2007 | Brink |
| 2008/0004536 A1 | 1/2008 | Baxi et al. |
| 2008/0004904 A1 | 1/2008 | Fran |
| 2008/0015454 A1 | 1/2008 | Gal |
| 2008/0021532 A1 | 1/2008 | Kveen et al. |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0097793 A1 | 4/2008 | Dicks et al. |
| 2008/0103402 A1 | 5/2008 | Stickney et al. |
| 2008/0167535 A1 | 7/2008 | Stivoric et al. |
| 2008/0177341 A1 | 7/2008 | Bowers |
| 2008/0183090 A1 | 7/2008 | Farringdon et al. |
| 2008/0221631 A1 | 9/2008 | Dupelle |
| 2008/0249591 A1 | 10/2008 | Gaw et al. |
| 2008/0287749 A1 | 11/2008 | Reuter |
| 2008/0287770 A1 | 11/2008 | Kurzweil et al. |
| 2008/0294019 A1 | 11/2008 | Tran |
| 2008/0306562 A1 | 12/2008 | Donnelly et al. |
| 2008/0312520 A1 | 12/2008 | Rowlandson et al. |
| 2008/0312522 A1 | 12/2008 | Rowlandson et al. |
| 2008/0312709 A1 | 12/2008 | Volpe et al. |
| 2009/0005827 A1 | 1/2009 | Weintraub et al. |
| 2009/0018428 A1 | 1/2009 | Dias et al. |
| 2009/0066366 A1 | 3/2009 | Solomon |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0082691 A1 | 3/2009 | Denison et al. |
| 2009/0093687 A1 | 4/2009 | Telfort et al. |
| 2009/0096417 A1 | 4/2009 | Idzik et al. |
| 2009/0118808 A1 | 5/2009 | Belacazar et al. |
| 2009/0138059 A1 | 5/2009 | Ouwerkerk |
| 2009/0146822 A1 | 6/2009 | Soliman |
| 2009/0177100 A1 | 7/2009 | Ternes |
| 2009/0212984 A1 | 8/2009 | Baker |
| 2009/0231124 A1 | 9/2009 | Klabunde et al. |
| 2009/0232286 A1 | 9/2009 | Hurwitz |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0281394 A1 | 11/2009 | Russell et al. |
| 2009/0287120 A1 | 11/2009 | Ferren et al. |
| 2009/0292194 A1 | 11/2009 | Libbus et al. |
| 2009/0295326 A1 | 12/2009 | Daynes et al. |
| 2009/0307266 A1 | 12/2009 | Fleizach et al. |
| 2009/0318779 A1 | 12/2009 | Tran |
| 2010/0010559 A1 | 1/2010 | Zhang et al. |
| 2010/0052892 A1 | 3/2010 | Allen et al. |
| 2010/0052897 A1 | 3/2010 | Allen et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0081962 A1 | 4/2010 | Hamaguchi et al. |
| 2010/0083968 A1 | 4/2010 | Wondka et al. |
| 2010/0102832 A1 | 4/2010 | Bartling et al. |
| 2010/0114243 A1 | 5/2010 | Nowak et al. |
| 2010/0171611 A1 | 7/2010 | Gao et al. |
| 2010/0179438 A1 | 7/2010 | Heneghan et al. |
| 2010/0198094 A1 | 8/2010 | Turicchia et al. |
| 2010/0234715 A1 | 9/2010 | Shin et al. |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0015533 A1 | 1/2011 | Cox et al. |
| 2011/0022105 A9 | 1/2011 | Owen et al. |
| 2011/0054264 A1 | 3/2011 | Fischell et al. |
| 2011/0077728 A1 | 3/2011 | Li et al. |
| 2011/0080294 A1 | 4/2011 | Tanishima et al. |
| 2011/0093840 A1 | 4/2011 | Pynenburg et al. |
| 2011/0098765 A1 | 4/2011 | Patel |
| 2011/0117878 A1* | 5/2011 | Barash ............. G08B 25/005 455/404.2 |
| 2011/0170692 A1 | 7/2011 | Konrad et al. |
| 2011/0172550 A1 | 7/2011 | Martin et al. |
| 2011/0196220 A1 | 8/2011 | Storm |
| 2011/0288604 A1 | 11/2011 | Kaib et al. |
| 2011/0288605 A1 | 11/2011 | Kaib et al. |
| 2011/0307284 A1 | 12/2011 | Thompson et al. |
| 2012/0011382 A1 | 1/2012 | Volpe et al. |
| 2012/0053479 A1 | 3/2012 | Hopenfeld |
| 2012/0112903 A1 | 5/2012 | Kaib et al. |
| 2012/0144551 A1 | 6/2012 | Guldalian |
| 2012/0146797 A1 | 6/2012 | Oskin et al. |
| 2012/0158074 A1 | 6/2012 | Hall |
| 2012/0158075 A1 | 6/2012 | Kaib et al. |
| 2012/0165684 A1 | 6/2012 | Sholder |
| 2013/0144355 A1 | 6/2013 | Macho et al. |
| 2013/0231711 A1 | 9/2013 | Kaib |
| 2013/0325078 A1 | 12/2013 | Whiting et al. |
| 2013/0325096 A1 | 12/2013 | Dupelle et al. |
| 2014/0012346 A1 | 1/2014 | Gilkerson et al. |
| 2014/0025131 A1 | 1/2014 | Sullivan et al. |
| 2014/0163334 A1 | 6/2014 | Volpe et al. |
| 2014/0206977 A1 | 7/2014 | Bahney et al. |
| 2014/0371806 A1 | 12/2014 | Raymond et al. |
| 2015/0005588 A1 | 1/2015 | Herken et al. |
| 2015/0039053 A1 | 2/2015 | Kaib et al. |
| 2015/0109125 A1 | 4/2015 | Kaib et al. |
| 2015/0217121 A1 | 8/2015 | Subramanian et al. |
| 2015/0231403 A1 | 8/2015 | Kaib et al. |
| 2015/0359490 A1 | 12/2015 | Massey et al. |
| 2016/0004831 A1 | 1/2016 | Carlson et al. |
| 2016/0023014 A1 | 1/2016 | Donnelly et al. |
| 2016/0143585 A1 | 5/2016 | Donnelly et al. |
| 2016/0278659 A1 | 9/2016 | Kaib et al. |
| 2016/0296125 A1 | 10/2016 | Volpe et al. |

(56) References Cited

U.S. PATENT DOCUMENTS

| | | | |
|---|---|---|---|
| 2016/0303371 A1 | 10/2016 | Whiting et al. | |
| 2017/0021184 A1 | 1/2017 | Pavel et al. | |
| 2017/0056682 A1 | 3/2017 | Kumar et al. | |
| 2018/0117348 A1 | 5/2018 | Kaib | |
| 2018/0235537 A1* | 8/2018 | Whiting | A61N 1/36564 |
| 2018/0353090 A1* | 12/2018 | Munaretto | A61B 5/026 |

FOREIGN PATENT DOCUMENTS

| | | |
|---|---|---|
| CN | 101848677 A | 9/2010 |
| DE | 102008026871 A1 | 12/2008 |
| EP | 0295497 B1 | 9/1993 |
| EP | 0335356 B1 | 3/1996 |
| EP | 1642616 A2 | 4/2006 |
| EP | 1455640 B1 | 1/2008 |
| EP | 1720446 B1 | 7/2010 |
| JP | S6368135 A | 3/1988 |
| JP | 5115450 A | 5/1993 |
| JP | H07541 A | 1/1995 |
| JP | H10-28679 A | 2/1998 |
| JP | H11319119 A | 11/1999 |
| JP | 2002-102361 A | 4/2002 |
| JP | 2002-514107 A | 5/2002 |
| JP | 2002200059 A | 7/2002 |
| JP | 2002534231 A | 10/2002 |
| JP | 2003235997 A | 8/2003 |
| JP | 2003260145 A | 9/2003 |
| JP | 2004538066 A | 12/2004 |
| JP | 2005275606 A | 10/2005 |
| JP | 2007531592 A | 11/2007 |
| JP | 2008513112 A | 5/2008 |
| JP | 2008302225 A | 12/2008 |
| JP | 2008302228 A | 12/2008 |
| JP | 2009510276 A | 3/2009 |
| JP | 2009510631 A | 3/2009 |
| JP | 2009518057 A | 5/2009 |
| JP | 2009-521865 A | 6/2009 |
| JP | 2009521260 A | 6/2009 |
| JP | 2009528909 A | 8/2009 |
| JP | 2010-508128 A | 3/2010 |
| JP | 2010530114 A | 9/2010 |
| WO | 200002484 A1 | 1/2000 |
| WO | 2004054656 A1 | 7/2004 |
| WO | 2004067083 A2 | 8/2004 |
| WO | 2004078259 A1 | 9/2004 |
| WO | 2005082454 A1 | 9/2005 |
| WO | 2006050235 A1 | 5/2006 |
| WO | 2006050325 A2 | 5/2006 |
| WO | 2006/059190 A2 | 6/2006 |
| WO | 2007019325 A2 | 2/2007 |
| WO | 20070057169 A1 | 5/2007 |
| WO | 2007077997 A1 | 7/2007 |
| WO | 2008137286 A1 | 11/2008 |
| WO | 2009034506 A1 | 3/2009 |
| WO | 2010014497 A1 | 2/2010 |
| WO | 2010025432 A1 | 3/2010 |
| WO | 2010077997 A2 | 7/2010 |
| WO | 2015127466 A2 | 8/2015 |

OTHER PUBLICATIONS

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

DeBock et al., "Captopril treatment of chronic heart failure in the very old," J. Gerontol. (1994) 49: M148-M152.

Extended European Search Report from corresponding European Application No. 11804401.5 dated May 18, 2016.

Harnett, P.R. et al., "A Survey and Comparison of Laboratory Test Methods for Measuring Wicking", Textile Research Journal, Jul. 1984.

International Search Report and Written Opinion from corresponding International Application No. PCT/US2011/059345, dated Jan. 25, 2012.

International Search Report and Written Opinion from PCT/US2013/028598 dated May 9, 2013.

International Search Report dated Nov. 21, 2011 from corresponding International Application No. PCT/US11/43360.

O'Keeffe et al., "Reproducability and responsiveness of quality of life assessment and six minute walk test in elderly heart failure patients," Heart (1998) 80: 377-382.

\* cited by examiner

| Prescriber: | [dropdown] ~1504 |

| Patient: | First Name [ ] MI [ ] Last Name [ ] |
| Patient Location: | Zip [ ] ~1508 |

| Insurance information: | [ ] ~1510 |

| Patient health information: | Provide details regarding patient underlying health condition and reason for device need |

| Length of Need: | [dropdown] ~1512 |

VT Threshold, BPM: 150    VF Threshold, BPM: 200    ~1516

Energy, Joules:  Shock 1: 150   Shock 2: 160   Shock 3: 180

Patient fitting location: [ ]

Prescriber Electronic Signature

Prescriber Login [ ]

Authorized e-signature [ ]

~1500

[ e-Order WCD ]
· Electronically submit medical order

Enter Order Information: [_____] [Search]

Prescriber Information
- Prescribing Physician: [_____] — 1604
- Prescribing Facility: [_____▼]
- Prescribing Address: [_____]
- Phone: [_____]

Patient Information — 1608
- Patient Name: [_____]
- Date of Birth: [_____]  Address: [_____]
- Phone: [_____]  Patient Sex [__]
- Does patient have a pace maker? If so, provide details. [_____]

Monitor Settings
- Underlying conditions to monitor: [Provide details: Bradycardia, tachycardia, pause, etc.]
- Send Monitor to Patient or issue in prescriber's office? [__]  [Provide details on type of service: continuous reports, weekly reports, daily reports, or end of use reports] — 1616
- Length of Need (days): [__] — 1612

Insurance Information — 1610
- Insurance Carrier: [_____]
- Policy Number: [_____]

Patient filling location details [_____]

1600

[Submit E-Order]

SYSTEMS AND METHODS FOR DEVICE INVENTORY MANAGEMENT AND TRACKING

CROSS-REFERENCE TO RELATED APPLICATION

This application claims priority under 35 U.S.C. § 119(e) to U.S. Provisional Application Ser. No. 62/738,262 titled "SYSTEMS AND METHODS FOR DEVICE INVENTORY MANAGEMENT AND TRACKING," filed Sep. 28, 2018, which is incorporated herein by reference in its entirety for all purposes.

TECHNICAL FIELD

The present disclosure is directed to systems and method for managing and tracking inventory of medical devices and related components and parts.

BACKGROUND

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. External cardioverters, defibrillators, and/or pacing devices such as manual defibrillators, automated external defibrillators (AEDs), or wearable cardioverter defibrillators (WCDs) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

There are a wide variety of electronic and mechanical devices for monitoring and treating patients' medical conditions. In some examples, depending on the underlying medical condition being monitored or treated, medical devices such as cardiac monitors or defibrillators can be prescribed to the patient. Physicians may use these medical devices alone or in combination with drug therapies to treat conditions such as cardiac arrhythmias.

Example external cardiac monitoring and/or treatment devices include cardiac monitoring devices such as the ZOLL® cardiac monitor, the ZOLL LifeVest® wearable cardioverter defibrillator, and the AED Plus, all available from ZOLL Medical Corporation.

Cardiac device and service providers as well as health care providers or their affiliates way maintain an inventory of medical devices that have been serviced, cleaned, their batteries charged, and, in some cases, configured before being deployed to patients.

SUMMARY

According to one aspect, an inventory management system for wearable cardiac devices includes a wearable cardiac device including an associated plurality of separate wearable cardiac device components stored as inventory at a first inventory location; a plurality of communication interface circuits associated with a corresponding one of the plurality of separate wearable cardiac device components and configured to facilitate transmission of inventory information through a network; at least one server device disposed at a central location and communicatively coupled to the network, the at least one server device including a processor, and a memory communicatively coupled to the processor and including instructions that when executed by the processor cause the processor to receive the inventory information from the plurality of communication interface circuits via the network; receive a prescription for a patient; retrieve one or more prescription parameters based on the prescription for the patient; locate, in the inventory information, the wearable cardiac device and the associated plurality of separate wearable cardiac device components based on the prescription parameters; determine a deployment status of the wearable cardiac device and the associated plurality of separate wearable cardiac device components; and select the wearable cardiac device for the patient including the plurality of the separate wearable cardiac device components on determining that the deployment status indicates that the wearable cardiac device and the associated plurality of separate wearable cardiac device components is ready to be deployed to the patient.

In one embodiment, the memory further includes instructions that when executed by the processor cause the processor to automatically configure the wearable cardiac device according to the one or more prescription parameters. In another embodiment, the memory further includes instructions that when executed by the processor cause the processor to display a user interface configured to allow a user to configure the wearable cardiac device.

In another embodiment, the wearable cardiac device is a wearable defibrillator. In a further embodiment, the one or more prescription parameters includes one or more treatment parameters for delivering therapy to treat a cardiac condition of the patient via the wearable defibrillator. In yet a further embodiment, the one or more treatment parameters includes at least one of a treatment energy level, a pulse count, a pulse duration, and a pulse frequency. In yet another embodiment, the associated plurality of separate wearable cardiac device components of the wearable defibrillator includes one or more of: a battery, a controller, a harness, a plurality of electrocardiogram (ECG) sensing electrodes, a plurality of treatment electrodes, a plurality of gel packets configured for use with at least one of the plurality of ECG sensing electrodes and the plurality of treatment electrodes, a holster for the controller, and one or more user manuals.

In one embodiment, the wearable cardiac device includes one of a mobile cardiac telemetry device and a mobile cardiac event monitor. In another embodiment, a second wearable cardiac device includes a second plurality of separate wearable cardiac device components stored as inventory at a second inventory location. In yet another embodiment, the memory further includes instructions that when executed by the processor cause the processor to receive a second prescription for a second patient; and identify for the second patient, based on the inventory information and the second prescription, the second wearable cardiac device including the second plurality of the separate wearable cardiac device components.

In one embodiment, the plurality of communication interface circuits includes at least one of a Bluetooth interface circuit, a Wi-Fi interface circuit, NFC interface circuit, an RFID interface circuit, and an RFID tag.

In another embodiment, the at least one server device is a first server device at the central location, the inventory management system further including at least one second server device disposed at the first inventory location and communicatively coupled to the network, the at least one second server device configured to receive, from the plurality of communication interface circuits, inventory information about at least one component of the plurality of separate wearable cardiac device components at the first location; and communicate, via the network, the inventory information to the at least one first server device at the central location. In a further embodiment, the inventory information includes at least one of an identifier of the at least one component, a type of the at least one component, a quantity of the at least one component, a status of the at least one component, a location of the at least one component within a depot, and an expiration date of the at least one component.

In another embodiment, the prescription includes at least one of a directive to monitor the patient, a directive to monitor and treat the patient, an identity of the patient, a medical condition of the patient, a harness measurement of the patient, and an operating parameter of the wearable cardiac device.

In another embodiment, the memory further includes instructions that when executed by the processor cause the processor to identify a medical service person to fulfill the prescription for the patient based on predetermined medical service person criteria, a status of the medical service person, and the prescription. In a further embodiment, the memory further includes instructions that when executed by the processor cause the processor to assign the medical service person to the patient to fulfill the prescription for the patient.

In one embodiment, the memory further includes instructions that when executed by the processor cause the processor to provide, via a user interface, status information about a selected one of the wearable cardiac device components.

In one embodiment, the plurality of separate wearable cardiac device components includes a plurality of separate reusable components and a plurality of separate disposable components. In a further embodiment, the memory further includes instructions that when executed by the processor cause the processor to provide, via a user interface, information about when a selected reusable component was last refurbished or is in need of refurbishment.

In another aspect, an inventory management server device at a central location and coupled to a network includes a processor, and a memory communicatively coupled to the processor and including instructions that when executed by the processor cause the processor to receive, via the network, inventory information from a plurality of communication interface circuits regarding a plurality of wearable cardiac devices each including a plurality of separate wearable cardiac device components stored as inventory at a first inventory location; receive a prescription for a patient; retrieve one or more prescription parameters based on the prescription for the patient; locate, in the inventory information, the wearable cardiac device and the associated plurality of separate wearable cardiac device components based on the prescription parameters; determine a deployment status of the wearable cardiac device and the associated plurality of separate wearable cardiac device components; and select the wearable cardiac device for the patient including the plurality of the separate wearable cardiac device components on determining that the deployment status indicates that the wearable cardiac device and the associated plurality of separate wearable cardiac device components is ready to be deployed to the patient.

In one embodiment, the memory further includes instructions that when executed by the processor cause the processor to automatically configure the wearable cardiac device according to the one or more prescription parameters. In another embodiment, the memory further includes instructions that when executed by the processor cause the processor to display a user interface configured to allow a user to configure the wearable cardiac device.

In another embodiment, the wearable cardiac device is a wearable defibrillator. In a further embodiment, the one or more prescription parameters includes one or more treatment parameters for delivering therapy to treat a cardiac condition of the patient via the wearable defibrillator. In a still further embodiment, the one or more treatment parameters includes at least one of a treatment energy level, a pulse count, a pulse duration, and a pulse frequency. In yet a further embodiment, the associated plurality of separate wearable cardiac device components of the wearable defibrillator includes one or more of: a battery, a controller, a harness, a plurality of electrocardiogram (ECG) sensing electrodes, a plurality of treatment electrodes, a plurality of gel packets configured for use with at least one of the plurality of ECG sensing electrodes and the plurality of treatment electrodes, a holster for the controller, and one or more user manuals.

In one embodiment, the wearable cardiac device includes one of a mobile cardiac telemetry device and a mobile cardiac event monitor. In another embodiment, a second wearable cardiac device including a second plurality of separate wearable cardiac device components stored as inventory at a second inventory location. In yet another embodiment, the memory further includes instructions that when executed by the processor cause the processor to receive a second prescription for a second patient; and identify for the second patient, based on the inventory information and the second prescription, the second wearable cardiac device including the second plurality of the separate wearable cardiac device components.

In one embodiment, the plurality of communication interface circuits includes at least one of a Bluetooth interface circuit, a Wi-Fi interface circuit, NFC interface circuit, an RFID interface circuit, and an RFID tag. In a further embodiment, the inventory information includes at least one of an identifier of the at least one component, a type of the at least one component, a quantity of the at least one component, a status of the at least one component, a location of the at least one component within a depot, and an expiration date of the at least one component.

In one embodiment, the prescription includes at least one of a directive to monitor the patient, a directive to monitor and treat the patient, an identity of the patient, a medical condition of the patient, a harness measurement of the patient, and an operating parameter of the wearable cardiac device.

In another embodiment, the memory further includes instructions that when executed by the processor cause the processor to identify a medical service person to fulfill the prescription for the patient based on predetermined medical service person criteria, a status of the medical service person, and the prescription. In a further embodiment, the memory further includes instructions that when executed by the processor cause the processor to assign the medical service person to the patient to fulfill the prescription for the patient.

In one embodiment, the memory further includes instructions that when executed by the processor cause the processor to provide, via a user interface, status information about a selected one of the wearable cardiac device components.

In another embodiment, the plurality of separate wearable cardiac device components includes a plurality of separate reusable components and a plurality of separate disposable components. In a further embodiment, the memory further includes instructions that when executed by the processor cause the processor to provide, via a user interface, information about when a selected reusable component was last refurbished or is in need of refurbishment.

In another aspect, a medical service personnel management system, the system includes an electronic device associated with a medical service person having access to a first location; a network interface disposed in the electronic device and configured to facilitate transmission of medical service personnel information through a network; at least one server device disposed at a central location and communicatively coupled to the network, the server device including a processor; a memory communicatively coupled to the processor and including instructions that, when executed by the processor causes the processor to receive the medical service personnel information from the network interface via the network; receive a prescription for a patient; retrieve one or more prescription parameters from the prescription for the patient; automatically analyze the one or more prescription parameters and the medical service personnel information to identify a medical service person to fulfill the prescription for the patient, and provide an output report indicating assignment of the identified medical service person to the patient to fulfill the prescription for the patient based on the analysis.

In one embodiment, the electronic device is one of a personal mobile device of the medical service person, a mobile device assigned to the medical service person, a tablet computing device, and a computer. In another embodiment, the electronic device is a multi-purpose electronic device including a dedicated application configurable to be uniquely associated with a medical service person. In another embodiment, the memory further includes instructions that when executed by the processor cause the processor to configure a wearable cardiac device according to the prescription.

In one embodiment, the memory further includes instructions that when executed by the processor cause the processor to display a user interface configured to allow a user to configure a wearable cardiac device. In another embodiment, the prescription includes one or more parameters for operating an external wearable cardiac treatment device by delivering therapy to treat a cardiac condition of the patient. In a further embodiment, the one or more parameters includes at least one of a treatment energy level, a pulse count, a pulse duration, and a pulse frequency. In another embodiment, the prescription includes at least one of a directive to monitor the patient, a directive to monitor and treat the patient, an identity of the patient, a medical condition of the patient, a harness measurement of the patient, and an operating parameter of the wearable cardiac device.

In one embodiment, the memory further includes instructions that when executed by the processor cause the processor to automatically analyze the one or more prescription parameters and the medical service personnel information to identify the medical service person based on at least one of schedule, availability, location, assigned territory, expertise, certifications, current or historic case load, urgency of the assignment, medical service personnel employment status, medical service personnel's prior patient feedback, medical service personnel's salary or reimbursement rate. In a further embodiment, the memory further includes instructions that when executed by the processor cause the processor to assign the medical service person to the patient to fulfill the prescription for the patient.

In another embodiment, the memory further includes instructions that when executed by the processor cause the processor to transmit to the electronic device via the network interface one of a location of the patient and navigation directions to the location of the patient from a current location of the mobile device. In another embodiment, the memory further includes instructions that when executed by the processor cause the processor to identify, based the prescription, a wearable cardiac device for the patient including a plurality of separate wearable cardiac device components at the first location. In another embodiment, the output report is provided on at least one of a user interface of a desktop computer, a user interface of a smartphone, and a user interface of a tablet.

In another aspect, a medical service personnel management server device at a central location and coupled to a network includes a processor; a memory communicatively coupled to the processor and including instructions that, when executed by the processor causes the processor to receive, via the network, medical service personnel information regarding a plurality of medical service persons at a plurality of geographical locations; receive a prescription for a wearable cardiac device patient; retrieve one or more prescription parameters from the prescription for the patient; automatically analyze the one or more prescription parameters and the medical service personnel information to identify the medical service person to fulfill the prescription for the patient; and provide an output report indicating assignment of the identified medical service person to the patient to fulfill the prescription for the wearable cardiac device patient based on the analysis.

In one embodiment, the memory further includes instructions that when executed by the processor cause the processor to configure a wearable cardiac device according to the prescription. In another embodiment, the memory further includes instructions that when executed by the processor cause the processor to display a user interface configured to allow a user to configure a wearable cardiac device.

In another embodiment, the prescription includes one or more parameters for operating an external wearable cardiac treatment device by delivering therapy to treat a cardiac condition of the patient. In a further embodiment, the one or more parameters includes at least one of a treatment energy level, a pulse count, a pulse duration, and a pulse frequency. In a further embodiment, the prescription includes at least one of a directive to monitor the patient, a directive to monitor and treat the patient, an identity of the patient, a medical condition of the patient, a harness measurement of the patient, and an operating parameter of the wearable cardiac device.

In one embodiment, the memory further includes instructions that when executed by the processor cause the processor to automatically analyze the one or more prescription parameters and the medical service personnel information to identify the medical service person based on at least one of schedule, availability, location, assigned territory, expertise, certifications, current or historic case load, urgency of the assignment, medical service personnel employment status, medical service personnel's prior patient feedback, medical service personnel's salary or reimbursement rate. In a further embodiment, the memory further includes instructions that when executed by the processor cause the processor to assign the medical service person to the patient to fulfill the prescription for the patient.

In another embodiment, the memory further includes instructions that when executed by the processor cause the processor to transmit to the electronic device via the network interface one of a location of the patient and navigation directions to the location of the patient from a current location of the mobile device. In one embodiment, the memory further includes instructions that when executed by the processor cause the processor to identify, based the prescription, a wearable cardiac device for the patient including a plurality of separate wearable cardiac device components at the first location.

In another embodiment, the output report is provided on at least one of a user interface of a desktop computer, a user interface of a smartphone, and a user interface of a tablet.

In another aspect, an electronic device for use by a medical service person includes a network interface configured to facilitate transmission of wearable cardiac device inventory information and a prescription of a wearable cardiac device patient through a network; a graphical user interface; a processor; and a memory communicatively coupled to the processor and including instructions that when executed by the processor causes the processor to receive from a medical service person, via a graphical user interface of the electronic device, an availability status of the medical service person to indicate if the medical service person is available to accept new prescriptions; transmit the availability status of the medical service person associated with the electronic device; receive, via the network interface of the electronic device, one or more prescription parameters of a wearable cardiac device patient based on a prescription received at a central server and in response to the transmitted availability status of the medical service person; and receive, via a network interface of the electronic device, inventory information regarding a wearable cardiac device and associated plurality of separate wearable cardiac device components that is identified for the wearable cardiac device patient based on the one or more prescription parameters; format the received one or more prescription parameters and inventory information regarding a wearable cardiac device and associated plurality of separate wearable cardiac device components that is identified for the wearable cardiac device for display on the user interface of the mobile device to the medical service person; and display, on the graphical user interface of the mobile device, the formatted one or more prescription parameters and inventory information regarding a wearable cardiac device and associated plurality of separate wearable cardiac device components.

In one embodiment, the memory further includes instructions that when executed by the processor cause the processor to transmit, via the network interface, medical service person status information. In a further embodiment, the medical service person status information includes an indication of at least one of: that the medical service person is available to accept new prescriptions, that the medical service person is not available to accept new prescriptions. In yet a further embodiment, the medical service person status information includes a geographical location of the medical service person.

In another embodiment, the prescription of the wearable cardiac device patient includes a prescription of a wearable defibrillator for the patient. In yet another embodiment, the memory further includes instructions that when executed by the processor cause the processor to automatically configure a wearable cardiac device according to the prescription.

In one embodiment, the memory further includes instructions that when executed by the processor cause the processor to display, on the user interface, a control allowing the medical service person to configure a wearable cardiac device. In another embodiment, the electronic device includes one of a multipurpose computing device, a tablet, a smartphone, and a personal digital assistant.

In another aspect, a non-transitory computer-readable medium has stored thereon computer-executable instructions that, when executed by one or more processors on a mobile device, cause the one or more processors to receive from a medical service person, via a graphical user interface of the mobile device, an availability status of the medical service person to indicate if the medical service person is available to accept new prescriptions; transmit the availability status of the medical service person associated with the mobile device; receive, via the network interface of the mobile device, one or more prescription parameters of a wearable cardiac device patient based on a prescription received at a central server and in response to the transmitted availability status of the medical service person; receive, via a network interface of the mobile device, inventory information regarding a wearable cardiac device and associated plurality of separate wearable cardiac device components that is identified for the wearable cardiac device patient based on the one or more prescription parameters; format the received one or more prescription parameters and inventory information regarding a wearable cardiac device and associated plurality of separate wearable cardiac device components that is identified for the wearable cardiac device for display on the user interface of the mobile device to the medical service person; and display, on the graphical user interface of the mobile device, the formatted one or more prescription parameters and inventory information regarding a wearable cardiac device and associated plurality of separate wearable cardiac device components.

In one embodiment, the availability status of the medical service person includes an indication that the medical service person is not available to accept new prescriptions. In another embodiment, the computer-executable instructions further causes the one or more processors to transmit a geographical location of the medical service person. In yet another embodiment, the prescription of the wearable cardiac device patient includes a prescription of a wearable defibrillator for the patient.

In one embodiment, the computer-executable instructions further cause the one or more processors to automatically configure a wearable cardiac device according to the prescription. In another embodiment, the computer-executable instructions further cause the one or more processors to display, on the graphical user interface, a control allowing the medical service person to configure a wearable cardiac device. In another embodiment, the mobile device includes one of a multipurpose computing device, a tablet, a smartphone, and a personal digital assistant.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 15 is an example prescription or electronic order interface for a wearable treatment device; and FIG. 16 is an example prescription or electronic order interface for wearable monitoring device.

DETAILED DESCRIPTION

Overview

Figure 1A:
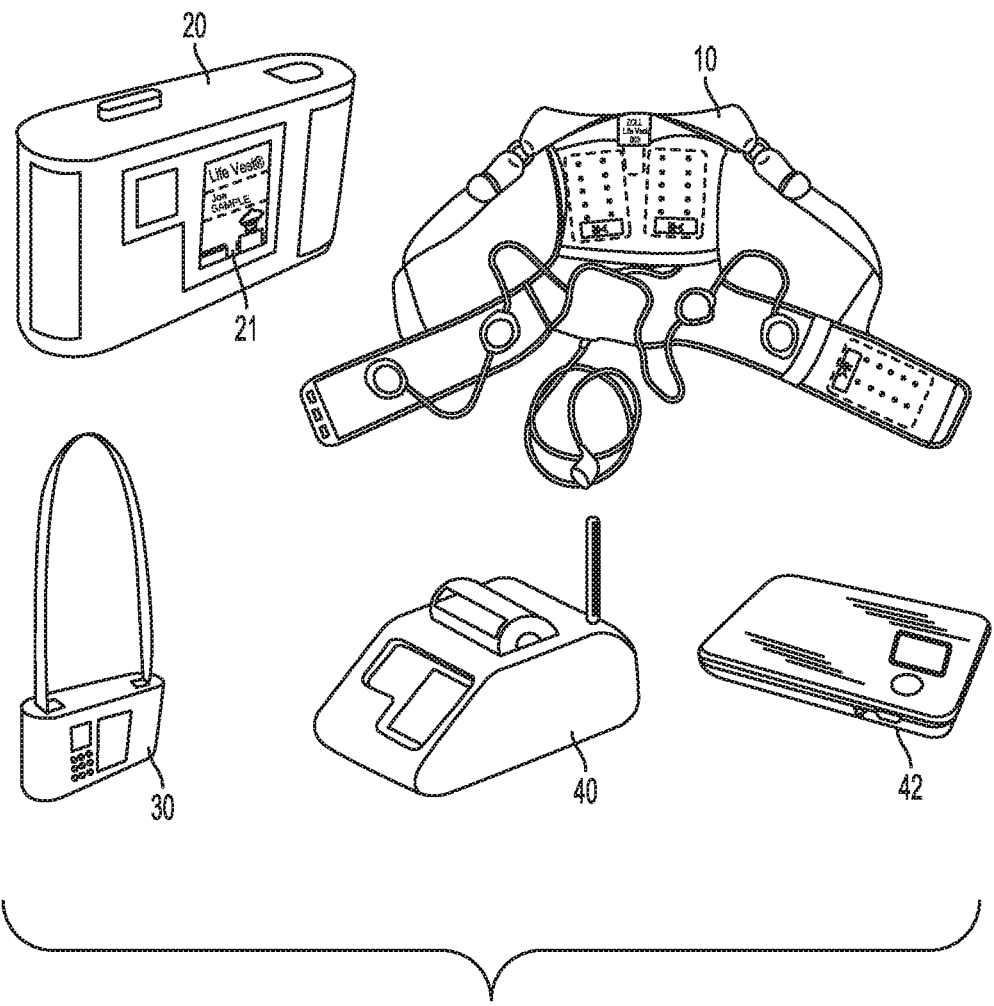
FIG. 1A illustrates examples of medical devices and components for use with the disclosed systems.

A variety of medical devices may be prescribed or otherwise assigned to patients needing monitoring or treatment from such devices. For example, a patient being sent home from the hospital following a confirmed or suspected cardiac event may be provided with a cardiac monitoring or treatment device, such as a cardiac monitoring device or a wearable defibrillator. For example, heart failure patients may be enrolled within a heart failure and arrhythmia management system. Such a system can include a portable and/or wearable patient monitoring device configured for continuous monitoring of a patient's cardiac and other vital physiological information. For example, the device can monitor ECG signals, transthoracic impedance, pulse oxygen, and thoracic fluid status over the monitoring period.

As described above, cardiac device and service providers, as well as health care providers or their affiliates can maintain an inventory of medical devices that have been serviced, cleaned, batteries charged as appropriate, and pre-configured before being deployed to patients. For example, the device may need to be configured specifically to the patient's medical monitoring needs as described in further detail below. What's more, different versions and configurations of such devices and their components may be maintained. Further, certain medical devices include components that may be consumable or disposable (e.g., garments or patches associated with wearable devices that may be discarded after use) or may be reusable (e.g., monitoring and/or treatment hardware). For instance, certain reusable components may be refurbished prior to be deployed once again into the inventory. As such, systems and methods described herein can be used to monitor devices, their components, how many of each kind are in stock and ready to be used by patients or medical service persons. Such systems and methods can also provide information regarding how many of such devices and/or components are near the end of the refurbishment pipeline and how soon they might be ready to be used by patients or medical service persons. For some components, such as disposable components that are garments for retaining medical components (e.g., a harness for a cardiac monitor), a range of garment sizes must be maintained.

While a patient may be prescribed a medical device for several weeks or more, there may also be a need to change out malfunctioning or depleted components during that time period. For example, a cardiac patient whose wearable defibrillator battery cannot hold a charge may need urgent service. Less urgent issues may also arise, such as a need to upgrade the firmware of a device deployed to a patient.

For these reasons, it is advantageous to maintain a depot (or multiple, geographically distributed depots) with an automated inventory management system for tracking medical devices and components within a reasonable proximity of a given patient. Such an automated inventory management system tracks the inventory of such medical devices and components as they cycle in and out of service with patients, and tracks (as well as anticipates) when such devices and components are due to be cycled out. Such a system maintains an up-to-date record or inventory of the devices and components currently at a depot location, along with their statuses, types/versions, and sizes, among other data.

Just as important as the devices are the medical service personnel trained to access and service those devices, deploy them to patients, train patients on the use of those devices, and ultimately recover and redeploy the devices to other patients. Devices, systems, and methods are described herein for, among other things, automatically identifying the best medical service person for the job based on their location, schedule, and/or expertise; scheduling an appointment between medical service person and patient; determining the particular device to be assigned to the patient; and retrieving the device from the depot en route to the patient.

This disclosure relates to an improved, automated inventory management system for medical devices, including wearable cardiac devices. A number of devices and/or components may be stored as inventory at one or more geographically distributed depots or warehouses, waiting to be deployed to patients. Each device and/or component may incorporate a wireless component (such as an RFID tag, an NFC device, or a Bluetooth® module) that communicates via such short-range communications protocol or interface with a depot device at the warehouse, making information such as the medical device's status, specific location (e.g., within a room, shelf, bin, etc.), type, and other information available to the depot device. A server at a central location communicates with one or more depot devices at one or more depot locations via a long-range communications protocol or network interface (e.g., local area network (LAN), Internet Protocols (IP, IPv4, IPv6), or wireless or cellular wireless transmission protocols such as 802.11, WLAN, WPA, WEP, Wi-Fi, 2G, 3G, 4G, 5G, Long Term Evolution (LTE, LTE-M) standards, among others). For instance, the central location server may be located at a predetermined geographical main location deemed to oversee a predetermined grouping of depot devices at various geographically distributed depots. The central location server receives inventory information from the depot devices. The central location server may receive a prescription or electronic order for a patient and, based on the inventory information and the prescription, may automatically identify one or more medical devices to be assigned to the patient. Data may be transmitted among components in file formats including Javascript Object Notation (JSON), Extensible Markup Language (XML), or the like.

This disclosure further relates to a medical service personnel management system, in which a medical service person can receive and accept assignments of patients via an electronic mobile device, such as a smart phone, a smart watch, or a tablet. The mobile device has a network interface allowing it to communicate with a central server, for example, over a long-range wireless transmission protocol. In this manner, the central server can receive the medical service person's status, such as whether they are currently accepting new assignments, or their location. Upon receiving a prescription of a medical device for a patient, the central server can identify, based on the medical service person's status, the patient's prescription, and/or other criteria, that the medical service person may be suitable for fulfilling the prescription. For example, as described in further detail below, the criteria can include the medical service person's schedule, availability, location, assigned territory, expertise, certifications, current and/or historic case load, urgency of the assignment, employment status, prior patient feedback, salary or reimbursement rate, and the like.

The central server can parse a received prescription for a medical device and extract a plurality of relevant prescription parameters for analysis. Such prescription parameters can include a type of the medical device, the patient's underlying medical condition, the patient's age, gender, and other identifying characteristics and biometric information, a duration of wear of the medical device, monitoring and/or treatment settings for the device, the patient's size and fit (e.g., for garment(s) to be worn with the device), the location of the patient, and the patient's personal preferences, if any. The server can analyze the prescription parameters and automatically identify one or more medical devices and associated configuration settings for the devices. The patient assignment is then offered to the medical service person via the mobile device. If the assignment is accepted, the patient is assigned to the medical service person, who receives additional details regarding the patient and the prescription. For example, the server can then transmit information to the medical service person's mobile device regarding the identified one or more medical devices and associated configuration settings to the medical service person for confirmation of the appropriate device and associated settings.

This disclosure further relates to an electronic mobile device, and to a mobile application executing on such a device, for use by a medical service person in viewing and managing inventory of medical devices at one or more depot locations, and viewing patient prescriptions. The electronic device may transmit and receive inventory information, as well as patient prescription parameters, over a network. A graphical user interface allows the medical service person to view the inventory information and to assign medical devices to patients that have been prescribed the devices, and to replace the devices in inventory following the end of the prescription. The electronic device may also allow the medical service person to view the status of a device currently assigned to a patient.

Example Environment and Components

Figure 1B:
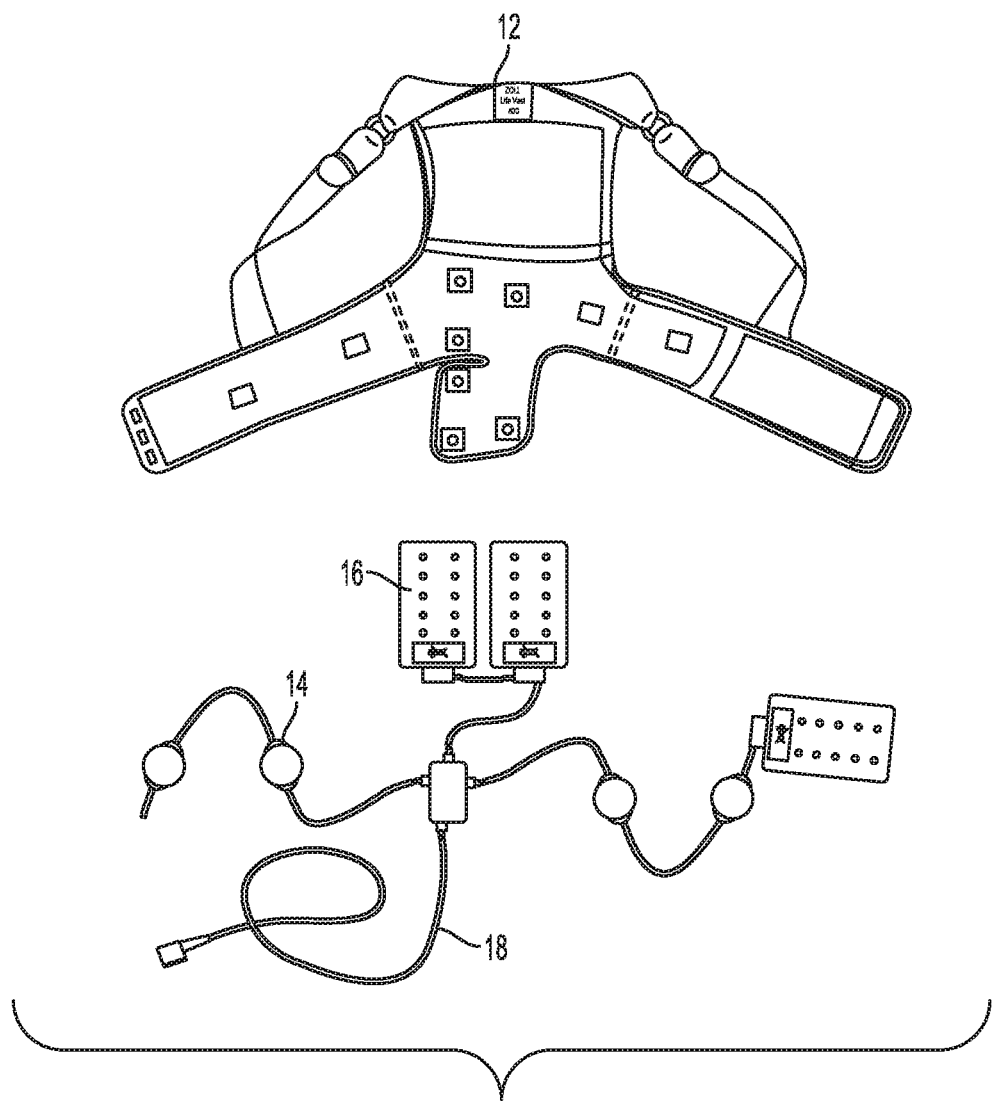
FIG. 1B illustrates examples of medical devices and components for use with the disclosed systems.

Example medical devices and components to be inventoried, transferred, tracked, and prescribed in some implementations are shown in FIGS. 1A and 1B. In one example, such medical devices may be of a type that is bodily-attached to a patient. Example external cardiac monitoring and/or treatment devices include mobile cardiac monitors and mobile cardiac telemetry devices, heart failure and/or arrhythmia management and/or monitoring devices, the ZOLL LifeVest® wearable cardioverter defibrillator, and the AED Plus, all available from ZOLL Medical Corporation. Such patient monitoring and/or treatment devices may be worn continuously by a patient to monitor a patient's physiological signals for abnormalities over an extended period of time, such as 10, 30, or 90 days, depending on the patient's needs and/or their physician's prescription. For example, the device may be configured to monitor for ECG abnormalities or thoracic fluid changes over time. In some examples, such devices may be worn nearly continuously, being removed only for cleaning, replacement of components, service, or the like. The devices may be affixed via a replaceable patch to the patient's skin. For example, they may be worn around the patient's neck and coupled to the patient via a plurality of ECG electrodes.

A garment and electrode belt assembly 10 for use in such a device is shown in FIG. 1A. The garment and electrode belt assembly 10 fit around a patient's body (e.g., the torso) and can be connected to a monitor 20. In some examples, the garment and electrode belt assembly 10 may be formed or treated with a waterproof or water-resistant material, such as rubber, neoprene, polyvinyl chloride (PVC), polyurethane (PU), silicone elastomer, fluoropolymers, or the like, and constructed in a manner allowing the medical device to be usable in wet environments (e.g., in a shower or a bath, or while swimming).

The monitor 20, being electronically coupled to one or more electrodes in the electrode belt 10, may be configured to monitor a heart rhythm of a patient wearing the device. The monitor 20 contains a battery or other power source that powers components of the monitor 20, such as a processor (e.g., within the monitor 20) or user display 21. In some examples, where the medical device is a cardioverter defibrillator, the monitor 20 may include a power source such as a battery to provide sufficient charge to provide one or more defibrillating shocks (e.g., up to ten shocks) or a plurality of lower-energy (e.g., pacing or transcutaneous electrical nerve stimulation (TENS)) pulses via one or more treatment electrodes of the garment and electrode belt assembly 10. A holster 30 may be used to retain and protect the monitor 20. In certain configurations, the holster 30 may provide a handle, strap, belt, or other feature allowing the holster 30 and the monitor 20 to be carried, restrained or mounted in a fixed position. The holster 30 allows the monitor 20 to be carried around by the patient while being protected from shock, the elements, and other environmental factors. While a holster 30 is shown and described herein, a variety of other holding or carrying equipment may be provided to the patient and may be similarly inventoried, transferred, tracked, and/or prescribed.

A charger 40 is configured to dock with and charge the battery of the monitor 20. In some examples, the charger 40 also includes a short-range or long-range network interface (e.g., Wi-Fi or Bluetooth® communications interface) allowing for communication with one or more external systems and/or entities, such as a medical care provider of the patient or a manufacturer of the medical device. When the monitor 20 is docked with the charger 40, the monitor 20 may transmit information about the device and/or the patient, via the network interface of the charger 40, to the external system. In other examples, the charger 40 may not incorporate a network interface, and may solely function as a charger.

The medical device may communicate with external systems via an access point such as a hotspot device 42, either in addition to or as an alternative to any long-range communications facilitated via the charger 40. For example, the hotspot device 42 may be an ad hoc wireless access point that is created by a dedicated hardware device or a smartphone feature that shares the phone's cellular data. Such a hotspot device 42 may be capable of pairing with one or more medical devices prescribed to a patient in an ad hoc manner, e.g., whenever medical device data from one or more devices worn by a patient needs to be transferred to a monitoring center. Alternatively or in addition, the hotspot device 42 may be configured to be uniquely paired with a particular medical device to be prescribed to a patient prior to deployment. The hotspot device 42 may require a data plan, and may access cellular signals and convert, e.g., 4G, 5G, LTE, LTE-M signals to Wi-Fi® protocol signals and vice versa, creating mobile Wi-Fi networks that can be used by one or medical devices within about 10 meters of the hotspot device 42.

The hotspot device 42 may be a stationary device (e.g., a tabletop device at a patient's home) or may be a mobile device. For example, the hotspot device 42 may be a dedicated electronic device providing connectivity via a network (e.g., the Internet using one or more Internet Protocols) and may be located at the patient's home, work, or other location, or may be a multi-purpose electronic device (e.g., a smartphone). Such a mobile device may create a mobile hotspot through tethering, transmitting data to and from the medical device via the mobile device's existing cellular data connection.

The external system and/or entity that receives physiological information from the medical devices can be a monitoring center for receiving physiological information regarding a patient, and responding to medical emergencies, identifying life-threatening premonitory condition that places a patient at elevated risk of developing a medical emergency, or generating reports for prescribing physicians based on the physiological information. For example, such a monitoring center can be an independent diagnostic testing facility (IDTF) within the scope of 42 CFT 410.33(a)(1). For instance, such a monitoring facility can be independent of either an attending or consulting physical's office or of a hospital. The facility may be a fixed location or a mobile entity.

It will be appreciated that the methods and systems described here for tracking medical devices can be applied to individual components and subcomponents of such devices as well. Such components and subcomponents may include replacement components, consumables or disposable parts, and/or reusable parts. For example, reusable parts may be configured to be refurbishable and re-deployed back into inventory. In the example shown in FIG. 1B, subcomponents of the garment and electrode belt assembly 10 of FIG. 1A may be individually tracked. For example, the garment and electrode belt assembly 10 may include individually trackable components such as the garment 12, one or more sensing electrodes 14, one or more treatment electrodes 16, and one or more connector cables 18. As discussed in more detail below, the system may track inventory of one or more complete devices (e.g., LifeVest® wearable cardioverter defibrillator), one or more components for such devices (e.g., a complete garment and electrode belt assembly 10), and/or one or more individual subcomponents of such components or devices. Components or medical devices as described herein can include, for example, assembled or unassembled complete devices, components thereof, or subcomponents thereof.

Disposables can include portions of the medical device that may be designed and/or intended for single use, use over a relatively short period of time, or use by a patient for the duration of the patient's prescription after which the portion may be discarded. Such disposables can be inventoried, tracked, transferred, and prescribed in a similar manner as the devices, components, and subcomponents as described herein. For instance, a stock of adhesive patches may be supplied along with a cardiac monitor configured to be adhesively mounted on a patient's skin for a period of time. In one configuration, an adhesive patch can be designed, configured or intended for use for between about 30 minutes to about 4 hours, about 4 hours to about 1 day, about 1 day to about 7 days, about 7 days to about 14 days, about 14 days to about 30 days, or about 1 month to about 3 months. Regardless of the length of time, the patient may be instructed to periodically replace the patch from the stock of patches provided at the outset of the monitoring period.

In another example, a supply of disposable garments may be provided along with a WCD prescribed to a patient for an extended period of time. In a configuration, the garment can be designed, configured or intended for use for between about 30 minutes to about 4 hours, about 4 hours to about 1 day, about 1 day to about 7 days, about 7 days to about 14 days, about 14 days to about 30 days, or about 1 month to about 3 months. In some implementations, the garment may be designed, configured or intended to be worn for about 1 to 2 days, laundered to remove dirt and grime as well as restore elasticity, and worn again. Such a garment may be worn and laundered a number of times before the end of the prescribed period of wear. Such garments may then be discarded at the end of the prescribed period.

Disposables can include gel packets. In implementations, after a WCD has delivered a therapeutic shock to the patient, the gel within the electrode belt worn by the patient may be depleted. As the patient is advised to continue to wear the WCD after therapy and until the patient is safely in hospital care, it may be necessary to manually apply additional gel between the conductive therapy electrodes and the patient's skin. To deal with such cases, the patient can be provided with additional gel supplied in one or more gel packets that the patient, an emergency medical responder, or other person can apply between the conductive therapy electrodes and the patient's skin. Such gel packets can be inventoried in a similar manner as other medical components described herein.

Figure 2:
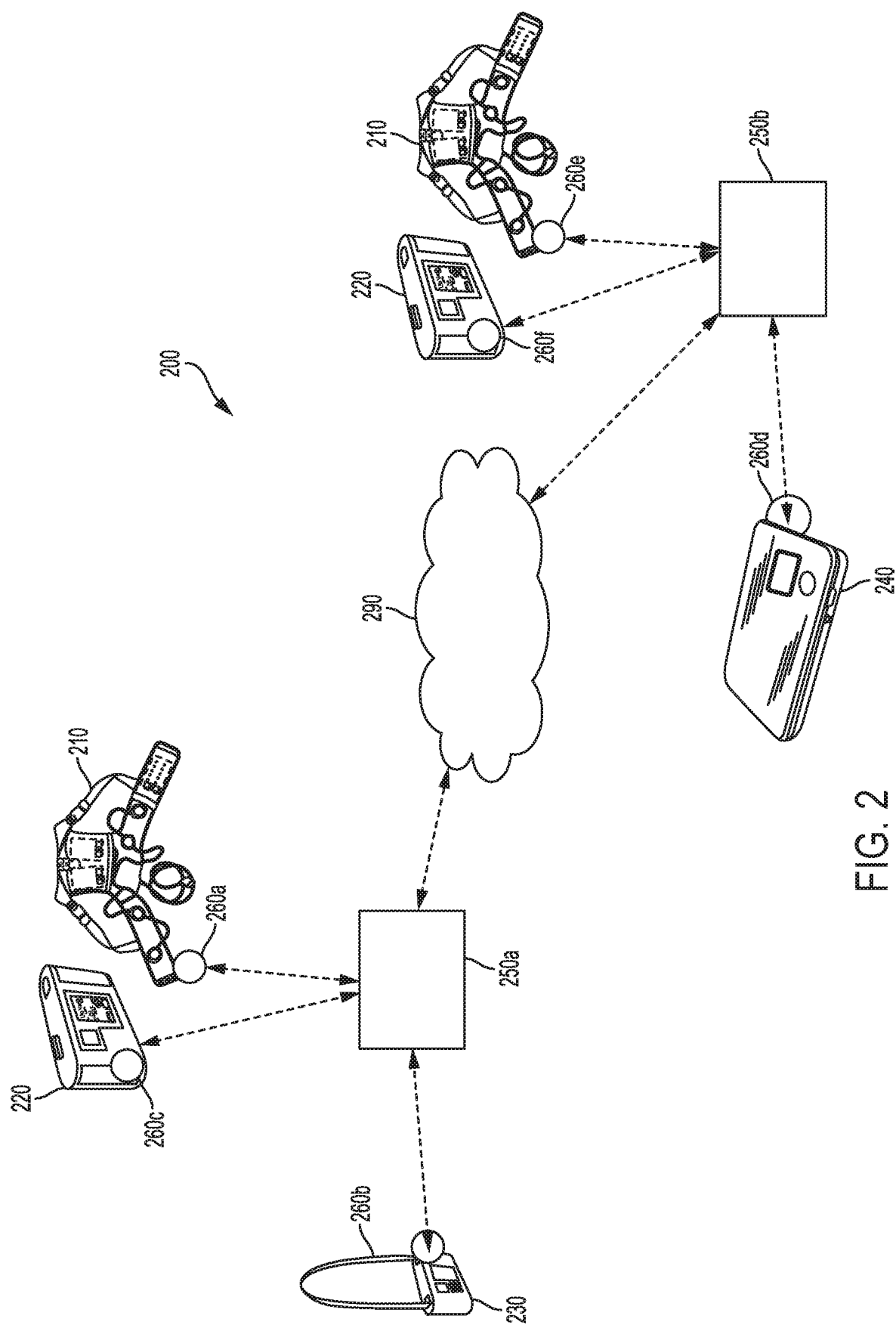
FIG. 2 is a block diagram of an example system for tracking inventory.

An example inventory tracking system 200 for tracking medical devices, components, subcomponents, and disposables inventory is shown in FIG. 2. Receivers 250a, 250b are configured to detect one or more devices, components, subcomponents, and consumables or disposables 210-240 (all generally referred to herein as components for convenience) in proximity of the respective receivers 250a, 250b. Each of receivers 250a, 250b may be located at one or more locations where equipment not currently deployed to a patient is stored, repaired, and/or maintained. The receivers

250a, 250b may be in communication with each other or other systems (e.g., a central server) via a network (e.g., the Internet).

Such depot locations may be geographically distributed in areas where such equipment is deployed to patients. For example, a depot location may be located to serve a particular neighborhood or district; area of a town or city; entire town or city; service area in which a medical provider or equipment provider operates; defined region; or other geographic designation. It will be appreciated, however, that some patients may be in proximity of more than one depot, and devices may be assigned to patients from any convenient depot based on the criteria discussed herein.

The receivers 250a, 250b may be configured to operate according to one or more short-range protocols (e.g., Bluetooth®, RFID, or NFC contactless protocols) and the one or more components 210-240 may each incorporate, or be affixed with, one or more tags 260a-f capable of communicating with the receivers 250a, 250b. For example, receiver 250a may receive information from a tag 260a affixed to a garment and electrode belt assembly 210. For example, the Bluetooth® interface signals can be processed by including Bluetooth® circuit(s) for establishing and managing the wireless communications and attendant data transfer mechanism. For example, the RFID information can be received and processed by RFID interface circuit(s) configured to establish and manage the RFID information received from RFID tags. For example, NFC interface circuit(s) can be included in the receivers 250a, 250b to receive and process data transfer in accordance with the NFC contactless protocol. As discussed in more detail below, the transmitted information from the devices and components may include the identity of the device or component with which the tag is associated, as well as information about the component itself, such as its type, size, and/or status.

Receivers 250a, 250b can include depot receivers that are components of, or in communication with, a server at a depot (e.g., a depot device), as discussed in more detail below. In RFID-based implementations, receivers 250a, 250b may have RFID based long and/or medium range RFID detection capabilities. For example, RFID based long-range capabilities can include RFID detection capabilities over 100 m-200 m (338-657 ft.) to interrogate active RFID tags that use predetermined frequencies (such as 2.45 GHz and 433 MHz frequencies). RFID-based medium-range capabilities can include RFID detection capabilities over 10 m-100 m (32-338 ft.) using, for example, UHF 865-868/902-928 MHz frequencies. Such receivers 250a, 250b can be configured to be installed at entrance, gate, door and corridor zones with respect to a depot. Such depot devices can, for example, support EPCglobal UHF Class 1 Gen 2/ISO 18000-6C protocol. As noted above, the receivers 250a, 250b can also support various communication interfaces such as Ethernet, Internet Protocol, and Wi-Fi 802.11 b/g. For example, such receivers 250a, 250b can include one or more antennas (e.g., a circularly polarized antenna) to effectively and expeditiously communicate information to a depot server or central server as the case may be.

In some implementations, receivers 250a, 250b can have an omni-directional antenna which can help enhance range. In some implementations, the receivers 250a, 250b can optionally include an external antenna to supplement the capabilities of an in-built antenna. For example, such RFID receivers can support RFID tags such as those compatible to 137005 RTLS series. The devices can include status indication LEDs that indicate standard device statuses such as RTL, RUN, BUS (busy), and ERR (error). Receivers 250a, 250b can have various communication interfaces such as Wi-Fi, USB, GPRS, Ethernet, RJ45, RS232, and RS 485. For example, the devices may have a direct mode and buffering mode. In direct mode, the device can upload messages to a host system in real time. In buffering mode, the device can save messages, which are uploaded only when requested by the host system. These RFID receivers have multi-detection capability and can read 100 tags per second.

The receivers 250a, 250b can be implemented as a single depot device or a distributed depot device system. For example, a distributed depot device system may include multiple such receivers 250a, 250b distributed about or within the depot and configured to wirelessly convey information to a local depot server device. The depot server device can then function as the main depot device authorized to communicate depot status information to the central server. For example, each of the depot devices housing the receivers 250a, 250b may have IP40, IP50, and IP64 ratings in accordance with Ingress Protection ratings defined in international standard EN 60529 (British BS EN 60529: 1992, European IEC 60509:1989), used to describe levels of sealing effectiveness of electrical enclosures against intrusion from foreign bodies (tools, dirt, etc.) and moisture. For example, the devices may be provided with plastic cover housing that allows for continued uninterrupted operation in a variety of environments, such as, high humidity (50-100%) wet (e.g., rain and/or storm-like conditions), and/or high temperatures (e.g., 90-165F). In some implementations, the depot devices can have an IP65 rating, providing protection from water ingress, dust ingress and physical shock.

Receivers 250a, 250b may be configured to communicate with each other or with external systems via a network 290. The network 290 may be a LAN or a WAN (e.g., the Internet), and may be a public network or a secure private network. Communications may be transmitted via TCP/IP or other protocol. Communications may be suitably encrypted, or may be carried out over a virtual private network (VPN) across a public network, enabling the receivers 250a, 250b to send and receive data across shared or public networks as if they were directly connected to a private network.

Example Inventory Management

Figure 3:
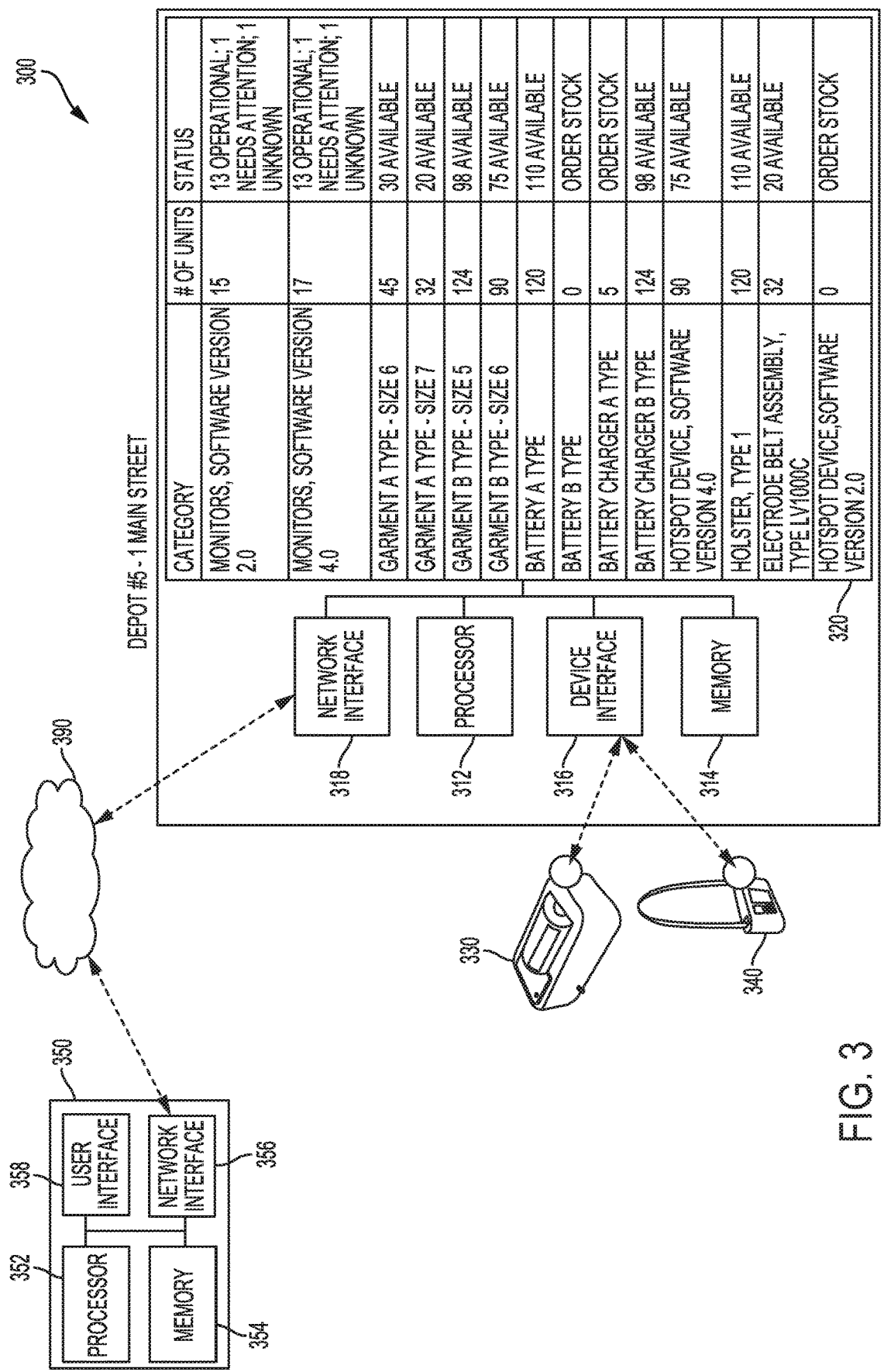
FIG. 3 is another block diagram of an example system for tracking inventory.

A block diagram of an example inventory tracking system 300 for tracking medical device components is shown in FIG. 3. The system 300 includes a central server 350 (for discussion herein, deemed as a first server) and a depot device 310 (deemed as a second server). In one example, the central server 350 is located at a central location, and the depot device 310 is located at a depot location, remote from the central location. In the example shown in FIG. 3, the depot location is at "Depot #5" on "1 Main Street" in an urban or suburban area near patients.

The central server 350 and the depot device 310 may be in communication via a network 390 (e.g., the Internet or a secure private network as described above). Information, such as prescription parameters, may be transmitted between the central server and the depot device 310 in data formats including JavaScript Objection Notation (JSON), Extensible Markup Language (XML), or other formats. The depot device 310 includes a receiver (e.g., receiver 250a as discussed above) configured to detect one or more medical device components in proximity of the depot device 310. The receiver may communicate with the one or more medical device components using a respective plurality of short-range communication interface circuits. As noted, the receiver may communicate with the medical device components using RFID, Bluetooth®, NFC, or Wi-Fi technology.

The central server 350 and the depot device 310 may communicate information to one another regarding medical device components stored and deployed from a depot location at which the depot device 310 is located.

The depot location may store medical device components of the type discussed above, and may allow users having access to the depot to configure those components and to retrieve or replace components that are being deployed to or returned by patients, respectively. In some examples, the depot device 310 may notify the central server 350 regarding the available inventory of medical devices and/or components at the depot location. Such notifications may be provided periodically, or upon request by the central server 350. For example, the central server 350 may receive the inventory information from the depot device 310, and may further receive a prescription for a patient requiring a wearable cardiac device. Having received the inventory information and prescription, the central server 350 may be configured to identify a wearable cardiac device (or components, subcomponents, and/or disposables/consumables therefor) for the patient associated with the prescription. The device thus having been assigned to the patient, the wearable cardiac device and/or components can be retrieved from the depot by medical personnel and delivered to the patient, and the depot device 310 updates its inventory accordingly. Alternatively or in addition, once a full set of devices, components, subcomponents, and consumables have been identified for a patient in accordance with a prescription, the central server 350 may relay instructions to the depot device 310 to cause the set to be shipped to the patient's location or location of a medical service person assigned to assist the patient.

The depot device 310 includes a processor 312, a memory 314, a device interface 316, and a network interface 318. The device interface 316 may be configured to communicate with one or more medical device components 330, 340 via a short-range wired or wireless protocol (e.g., RFID, NFC or Bluetooth®). The depot device 310 further includes an inventory storage 320 configured to store information about the medical device inventory on hand at the depot location. Such information may include identifiers of individual components (e.g., serial or inventory number), as well as their type (e.g., defibrillator), make, model, size, location within the depot (e.g., aisle, shelf, rack, etc. designated by a predetermined reference scheme), version (e.g., firmware version), expiration date, next service date, and deployment status. Deployment status may include, for example, whether the medical device and/or medical device components have been charged, cleaned, inspected, and/or serviced since it was last returned to the depot. For example, a deployment status can include a "needs attention" flag. Such an indicator may further specify the nature of the issue and what steps may need to be taken to clear the attention flag. For instance, the device may need new batteries, or may need to be recharged. A deployment status of "operational" or "available" can indicate that the device is ready to deploy to a patient. A deployment status of "order stock" may indicate that there are no devices or components in that category or class. An example of an inventory storage table 320 stored in a memory 314 is shown below in TABLE 1.

TABLE 1

| Category | Number of units | Deployment Status |
| --- | --- | --- |
| Monitors, software version 2.0 | 15 | 13 operational; 1 needs attention; 1 unknown |

TABLE 1-continued

| Category | Number of units | Deployment Status |
| --- | --- | --- |
| Monitors, software version 4.0 | 17 | 13 operational; 1 needs attention; 1 unknown |
| Monitors, software version 6.0 | 25 | 13 operational; 1 needs attention; 1 unknown |
| Garment A type - size 5 | 120 | 110 available |
| Garment A type - size 6 | 45 | 30 available |
| Garment A type - size 7 | 32 | 20 available |
| Garment B type - size 5 | 124 | 98 available |
| Garment B type - size 6 | 90 | 75 available |
| Garment B type - size 7 | 60 | 45 available |
| Battery A type | 120 | 110 available |
| Battery B type | 0 | Order stock |
| Battery charger A type | 5 | Order stock |
| Battery charger B type | 124 | 98 available |
| Hotspot device, software version 4.0 | 90 | 75 available |
| Hotspot device, software version 5.0 | 60 | 45 available |
| Holster, type 1 | 120 | 110 available |
| Electrode belt assembly, type LV1000A | 45 | 30 available |
| Electrode belt assembly, type LV1000C | 32 | 20 available |
| Hotspot device, software version 2.0 | 0 | Order stock |
| Hotspot device, software version 8.0 | 0 | Order stock |
| Holster, type 3 | 120 | 110 available |
| Electrode belt assembly, type LV1000B | 45 | 30 available |
| Electrode belt assembly, type LV1000D | 100 | 20 available |

The central server 350 includes a processor 352, a memory 354, a network interface 356, and a user interface 358. The central server 350 and the depot device 310 may each serve data to systems on a local area network (LAN) or a wide area network (WAN) over the Internet. The central server 350 and the depot device 310 may interact with each other and with other systems via a web server and/or file server application running on each, for the exchange of files or other data. The central server 350 and the depot device 310 may be rack-mounted servers, blade servers, or other types of servers. The central server 350 and the depot device 310 may each be scalable, that is, may incorporate (or have the capacity to incorporate) multiple processors 352 or memories 354. The central server 350 and the depot device 310 may each perform processing and storage entirely at the respective server, or may outsource some tasks, such as by storing data on the cloud. In some examples, the central server 350 may be a cluster of server devices. For example, the depot device 310 can use the HTTP methods POST and GET to transfer data to and from the central server 350. In this mode, devices can support HTTP authentication using the user name and password provided in a pre-stored settings file stored at the depot device 310.

The central server 350 may receive a prescription or new electronic order for one or more patients. The server 350 may parse the prescription or electronic order to store one or more prescription parameters in an associated database in device memory 354. Subsequently, responding to a request from a user, the server 350 may retrieve the one or more prescription parameters from the database and use that information to identify a suitable medical device or components therefor. The server 350 may further use that information to facilitate configuration of the medical device for the patient according to the prescription. For example, the prescription parameters can be input by a technician, a physician's assistant or other authorized person after a new medical order is received from an attending, consulting, or other physician responsible for the patient. The prescription parameters may be received at the network interface 356 of the central server 350 via the network 390. The prescription parameters may be provided to the central server 350 by an operator of the central server 350 or may be received remotely from the patient's health care provider, insurance company, or other source or intermediary.

Prescription Parameters

The prescription parameters or information retrieved from a server database in device memory 354 based on a new prescription or electronic order may include a general directive, such as whether the patient is to be monitored, monitored and treated. The prescription parameters may also include general information about the patient, including the patient's name or other identifier; the patient's age; the patient's address or other known or current location; the patient's size or other measurements for identifying a suitable medical device or components; and the patient's condition or diagnosis, and any related limits on the treatment. For example, the prescription parameters may include a limit on the amount of energy to be applied to an elderly patient during a pacing routine or for cardioverter and/or defibrillation. For example, the patient's size may be specified in the form of a predetermined proprietary format. For instance, the format may include use of an alphanumeric string where "A" is used for male patients, and "B" for female patients, and a number selected from within 1-10 to designate a garment size. For instance, A5 may be associated with a male patient, having shirt size 28, arm length 35.

The prescription parameters also include information about the types and parameters of treatment to be applied to the patient. For example, the prescription parameters may call for a wearable cardiac device to include one or more pacing or defibrillating routines to be applied in response to a respective cardiac event. If a cardiac event occurs for which pacing is a suitable response (e.g., tachycardia, bradycardia, or asystole), the prescription parameters may include parameters for applying pacing to that particular patient in response to a detected cardiac event. Such parameters may include treatment energy level (e.g., amplitude), a pulse count, a pulse duration, and a pacing pulse frequency. The prescription parameters may also include upper and lower thresholds (e.g., a beats per minute of the patient as measured in the patient's ECG signal) at which a particular treatment should be applied. For example, the pulse frequency at which to pace can be provided by prescription parameters, e.g., 5-200 pace pulses per minute, which is configurable. For example, other information that could be specified includes when the pacing would begin, e.g., in the event of bradycardia, when the measured heart rate falls below a threshold, e.g., 30 beats per minute averaged over 20 beats, or a combination of one or more ECG signal voltage readings and beats per minute (e.g. 1 mV, and 40 beats per minute).

For example, after identifying a ventricular fibrillation episode (VF), there may a response time of 25 seconds (programmable up to 55 seconds) to allow the patient time to respond to the alerts. The lower threshold for VF identification can be set from 120 to 250 beats per minute (bpm), with a default of 200 bpm. If the device identifies ventricular tachycardia (VT), there is a response time of 60 seconds (programmable up to 180 seconds). The lower threshold for VT identification can be set from 120 to the VF threshold, with a default setting of 150 bpm. A WCD device can deliver up to 5 defibrillating pulses during an arrhythmic episode. The energy of the pulses can be programmed individually to between 75 and 150 joules, with a default setting of 150 joules. Each of these parameters can be set within the prescription parameters, or a default value chosen. The prescription parameters can also include a previously gathered template of the patient's ECG and other bio-markers or physiological information. For instance, if a patient has previously had a WCD assigned, previously gathered baseline information may be on file for the patient which includes, e.g., an ECG morphology or other bio-marker templates. This previously gathered template information can be made available to the central server 350 as part of the prescription parameters.

In some implementation, where the medical device is a cardiac monitor (e.g., with no treatment elements or therapy capability) the prescription parameters can specify various threshold information for triggering alerts based on the underlying physiological information being monitored. For example, the cardiac monitor can be prescribed to monitor certain heart and arrhythmia conditions in the patient such as abnormal heart rates, abnormal morphologies, ventricular ectopic beats (VEBs), supraventricular ectopic beats (SVEBs), bradycardia, tachycardia, atrial fibrillation, heart pauses, ventricular runs, ventricular bigeminy, ventricular trigeminy, ventricular tachycardia, supraventricular tachycardia, 2nd Atrioventricular (AV) block, and 3rd Atrioventricular (AV) block.

As an example, the prescription parameters may include bradycardia thresholds as follows. A bradycardia onset heart rate can be specified in a range from 20 to 100 beats per minute, with a default value of around 40 beats per minute. When the patient's average heart rate (calculated over, e.g., 20 beats) drops below the value set by the prescription parameters, the cardiac monitor can report that the patient has entered bradycardia. A bradycardia offset heart rate can be specified in a range from 20 to 100 beats per minute, with a default value of around 45 beats per minute. When the patient is in bradycardia and the patient's average heart rate (calculated over, e.g., 20 beats) rises above the value set by the prescription parameters, the cardiac monitor can report that the patient has exited bradycardia. A bradycardia duration threshold can be specified in a range from 0 to 700 seconds, with a default value of around 30 seconds. The patient must remain in bradycardia for longer than the duration set by the value in this field before the cardiac monitor can report the event.

Similarly, as an example, the prescription parameters may include tachycardia thresholds as follows. A tachycardia onset heart rate can be specified in a range from 100 to 250 beats per minute, with a default value of around 120 beats per minute. When the patient's average heart rate (calculated over, e.g., 20 beats) rises above the value set by the prescription parameters, the cardiac monitor can report that the patient has entered tachycardia. A tachycardia offset heart rate can be specified in a range from 100 to 150 beats per minute, with a default value of around 110 beats per minute. When the patient is in tachycardia and the patient's average heart rate (calculated over, e.g., 20 beats) drops below the value set by the prescription parameters, the cardiac monitor can report that the patient has exited tachycardia. A tachycardia duration threshold can be specified in a range from 0 to 700 seconds, with a default value of around 30 seconds. The patient must remain in tachycardia for longer than the duration set by the value in this field before the cardiac monitor can report the event.

A patient must remain in atrial fibrillation for longer than an atrial fibrillation duration threshold set by the value in the prescription parameters before the cardiac monitor can report the event. For example, the atrial fibrillation duration threshold can be set between 0 and 60 minutes, with a default value of around 10 minutes. A patient must experience a heart pause with a duration greater than a heart pause duration set by the value in the prescription parameters before the cardiac monitor can report the event. For example, the heart pause duration threshold can be set between 1000 and 15000 seconds, with a default value of around 2500 seconds.

The central server 350 may facilitate configuration of the medical devices stored at the depot location. For example, the memory 354 of the central server 350 may store instructions allowing the processor 352 to automatically configure a wearable cardiac device according to a prescription of a patient to whom the device has been assigned. In another example, the central server 350 may generate instructions to be used by the depot device 310 to automatically configure the medical device. In yet another example, the central server 350 may generate instructions for manually configuring the medical device, which may be provided to a medical service person.

As noted above, the information used in configuring the medical device may include or relate to parameters used in applying pacing or defibrillation treatments to the patient, such as treatment energy level, a pulse count, a pulse duration, and a pulse frequency. Alternatively or in addition, the prescription parameters may also include or relate to which features or modules should be activated or provided on the medical device. For example, a patient prescribed a wearable cardiac device may be provided with a module configured to guide the patient through a rehabilitation or exercise program. The prescription parameters can include module configuration information for configuring the relevant module for the rehabilitation or exercise program. Alternatively or in addition, the patient may be required to perform a periodic assessment of the patient's psychomotor abilities or be administered surveys or health related questions via a user interface of the medical device. As an example, a periodic assessment may be implemented as a physical activity test. For instance, the patient may be prescribed a need to perform a WalkTest™ session as provided in WCDs from ZOLL Medical Corporation. For example, the device can monitor the patient as the patient walk for a predetermined duration, e.g., between 5 to 10 minutes. The device can monitor the patient's ECG, heart rate and other physiological information, and counts the number of steps taken. While the patient is walking, audible prompts indicate how much longer to walk, and when to stop walking. Before and after the walk test, the patient can be asked certain health related questions (e.g., about the patient's shortness of breath level and/or fatigue level). The patient's responses can be used to determine whether the walk test can be taken or suspended. The threshold for allowing the patient to take the walk test can be set by the patient's physician. The device can record the answers to the questions as well as the number of steps taken during the walk test and, during the next data transmission, send the results to the monitoring facility where the prescriber can review the results. The device can be programmed according to the patient's physician prescriber. For example, the prescription parameters can specify different schedules, either daily or weekly, and the number of times the walk is to be taken. The information can also set a threshold for answering the pre-session questions. If the patient answers the questions above a certain threshold, the device can be configured to not permit the patient to perform the session.

As another example, a periodic health survey may include questions regarding a range of health issues. The medical devices described herein can include an ability to ask the patient a series of prescriber selected health-related questions. The patient may be asked to answer the questions in a way that most closely describes how they feel. The patient proceeds to answer each question until all questions are answered. The medical device can store the patient's answers and, during the next data transmission, send the results to the remote entity where the prescriber can choose to review the results. A health survey can be enabled for different schedules, either daily or weekly, and the number of times the survey is to be taken. The prescription parameters can specify any of a number of questions, a schedule for when the survey should be administered, the specific questions and text to be administered to the patient, among other parameters.

Figure 4:
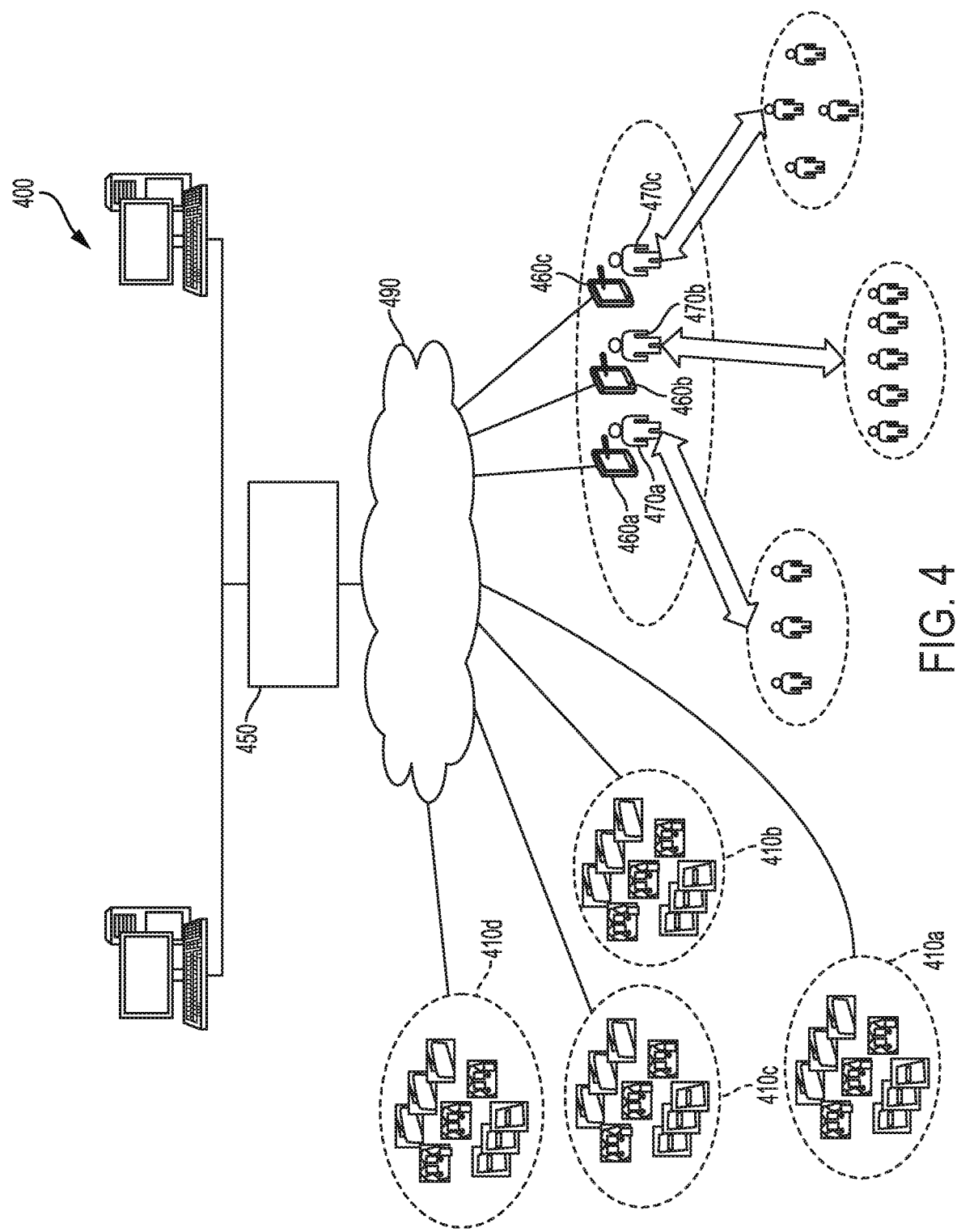
FIG. 4 is another block diagram of an example system for tracking inventory and managing medical service personnel.

A block diagram of a distributed medical device and component inventory network 400 is seen in FIG. 4. The inventory network 400 includes a central server 450 connected by a network 490 (e.g., the Internet) to a plurality of depot devices 410a-d located at depot locations geographically remote from one another (and possibly the central server 450). The central server 450 is further connected by the network 450 to one or more mobile devices 460a-d in the possession of a respective one or more medical service persons 470a-d. For example, a medical service person 470a may use mobile device 460a, which may be the medical service person's personal mobile device (e.g., smartphone or tablet), a mobile device assigned to the medical service person by their employer, or a dedicated device for performing the methods described herein. The mobile device 470a may be configured to execute a mobile application for performing such methods.

Medical service persons 470a-d may interact with patients 480 who have been prescribed medical devices, and may coordinate the assignment, delivery, maintenance, and eventual return of the medical device to a depot location once the prescription has expired. In one example, one or more patients 480 who have suffered a cardiac event, or are at risk of suffering one, may have been assigned a wearable cardiac device allowing the patient to be monitored (and possibly treated) in an outpatient manner.

In the example shown in FIG. 4, the central server 450 may receive a prescription for a patient 480b indicating that the patient 480b is to receive a particular type of wearable cardiac device. In response, the central server 450 requests and receives from a depot site (e.g., one associated with depot device 410b) inventory information at that depot location, including information indicative of whether the required device and components are at the depot location and available. If the necessary inventory is available at that depot location, the central server 450 may transmit to one or more medical service persons 470a-c a request that the equipment be retrieved from the appropriate depot location and delivered to the patient 480b, who may be, for example, at home or in the hospital waiting to be discharged. If a medical service person 470b accepts the request, the central server 450 transmits to mobile device 460b (associated with medical service person 470b) the prescription parameters and information about the patient, such as the patient's current location. The medical service person 470b may be instructed to proceed to the depot location and interact with the depot device located there (e.g., depot device 410b) and/or the equipment and components there in order to customize the necessary equipment for the patient. The medical service person 470b can then take possession of the equipment and deliver it to the patient 480b, and may provide instructions and further information to the patient 480b while doing so. In a similar manner, a medical service person 470a-c may be deployed by the central server 450 to retrieve malfunctioning or expired equipment; to retrieve equipment at the end of the patient's prescription; to periodically visit or communicate with the patient to determine if there are any issues with the equipment; or perform other similar tasks.

The depot location and associated depot device 410a-d and/or the medical service person 470a-c may be identified by the central server 450 for a particular patient and prescription based on any number of criteria, including the present location or assigned territory of the medical service person 470a-c; the schedule and availability of the medical service person 470-a-c; any expertise of the medical service person 470a-c; and the inventory at one or more depot locations, among other criteria.

Referring again to FIG. 3, a user can access the prescription parameters via the user interface 358 and select one or more medical devices, components, subcomponents, disposables, and/or other materials to fulfil the prescription. Alternatively, the user may assign the patient to a medical service person as described in further detail below. If the user is fulfilling the prescription at the central server, the user may be provided with additional screen layouts for displaying information from the inventory. For example, the user can select a particular cardiac monitor at a depot, e.g., Monitor Serial No. 555-666 located at warehouse on 23 Main St, Chelmsford, Mass., and request to view the particular monitor's status information. For example, such status information may include details regarding a remaining useful service life of the device, last refurbishment date, a current battery charge status, a description of available features, software version information, and software update status, among others. Similarly, the user can select a particular WCD monitor at the depot, e.g., WCD Serial No. 111-0089, and view the particular device status information. Similar to above, such status information may include details regarding a remaining useful service life of the WCD monitor, last refurbishment date, a current battery charge status, a description of available hardware and software features, software version information, software update status, among others. The user can also select associated disposable components that go with the WCD monitor, such as one or more garments, electrode belts, and gel packets. In some implementations, for reusable devices or components, the associated status information may indicate that the reusable device needs to be refurbished, and can provide details regarding a date by or time range within which the device is to be refurbished.

In some examples, the system 300 can be configured to automatically parse the patient's prescription and associate items from within the available inventory to fulfil the prescription. For example, as shown in Table 2 below for illustration, the system 300 may automatically parse a WCD prescription (column 1) and make choices from inventory and programming the device based on details within the prescription (column 2).

TABLE 2

| Prescription detail | Inventory item |
|---|---|
| Male, 42 inches, arm length 44 inches | A9 type garment, 2 nos. |
| WCD prescription, VT | Select WCD monitor and program in |

TABLE 2-continued

| Prescription detail | Inventory item |
|---|---|
| threshold 150 beats per minute, 5 pulses defibrillation, 125 joules, escalating | thresholds according to prescription |
| Monitor for other cardiac conditions | Activate cardiac arrhythmia monitoring (e.g., bradycardia, tachycardia, atrial fibrillation, and pause monitoring with standard thresholds) |
| Needs fluid monitoring | Activate thoracic fluid monitoring module |
| Cardiac rehabilitation routine recommended; periodic Walk Test ™ assessments | Include cardiac rehabilitation module Include WalkTest ™ module |
| Request periodic health status information | Activate Health Survey module |

Example Medical Service Personnel Management

Figure 5:
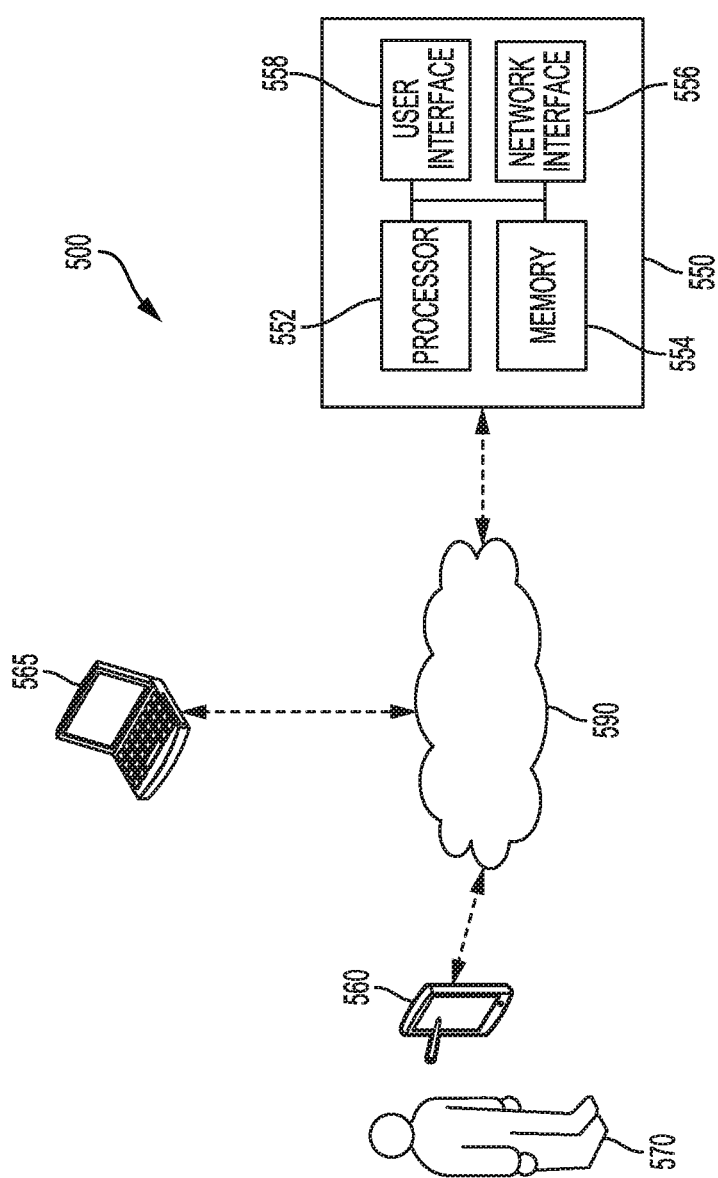
FIG. 5 is another block diagram of an example system for tracking inventory and managing medical service personnel.

A medical service personnel management system 500 is seen in FIG. 5. A medical service person 570 uses a mobile device 560 to interact, via a network 590, with a central server 550. In one example, the medical service person 570 uses the mobile device 560 to respond to a request to accept a new patient/prescription to be assigned a wearable medical device. If the request is accepted by the medical service person 570, the medical service person 570 is assigned the patient and provided the necessary information to fill the prescription. The central server includes a processor 552, a memory 554, a network interface 556, and a user interface 558. In some examples, one or more other devices 565 may interact with the central server 550 in a similar manner. The one or more other devices may be a desktop computer, laptop computer, or other secondary device of the medical service person 570, or may be a device associated with another user facilitating the interaction and fulfillment of the prescription, such as a colleague or supervisor of the medical service person 570.

The medical service person 570 may be medically trained, such as a physician, nurse, or physician's assistant. The medical service person 570 may also have received specialized training, such as from an operator of the system and/or a medical device company responsible for deploying and maintaining the medical devices.

The mobile device 560 used by the medical service person 570 may be a smartphone (e.g., an Apple iPhone or Motorola Android) or tablet device (e.g., an Apple iPad or Microsoft Surface) capable of performing additional functions in addition to those described herein, or may be a dedicated device for the applications described herein. The mobile device 560 may be a personal device owned by the medical service person 570, or may be loaned or otherwise assigned to the medical service person 570 by an employer or contractor. The mobile device 560 may include any number of components found in smartphone and other such mobile devices, including a user interface, memory, processor, location sensor (e.g., GPS), accelerometer, camera, microphone, telephone dialing, and the like.

Figure 6:
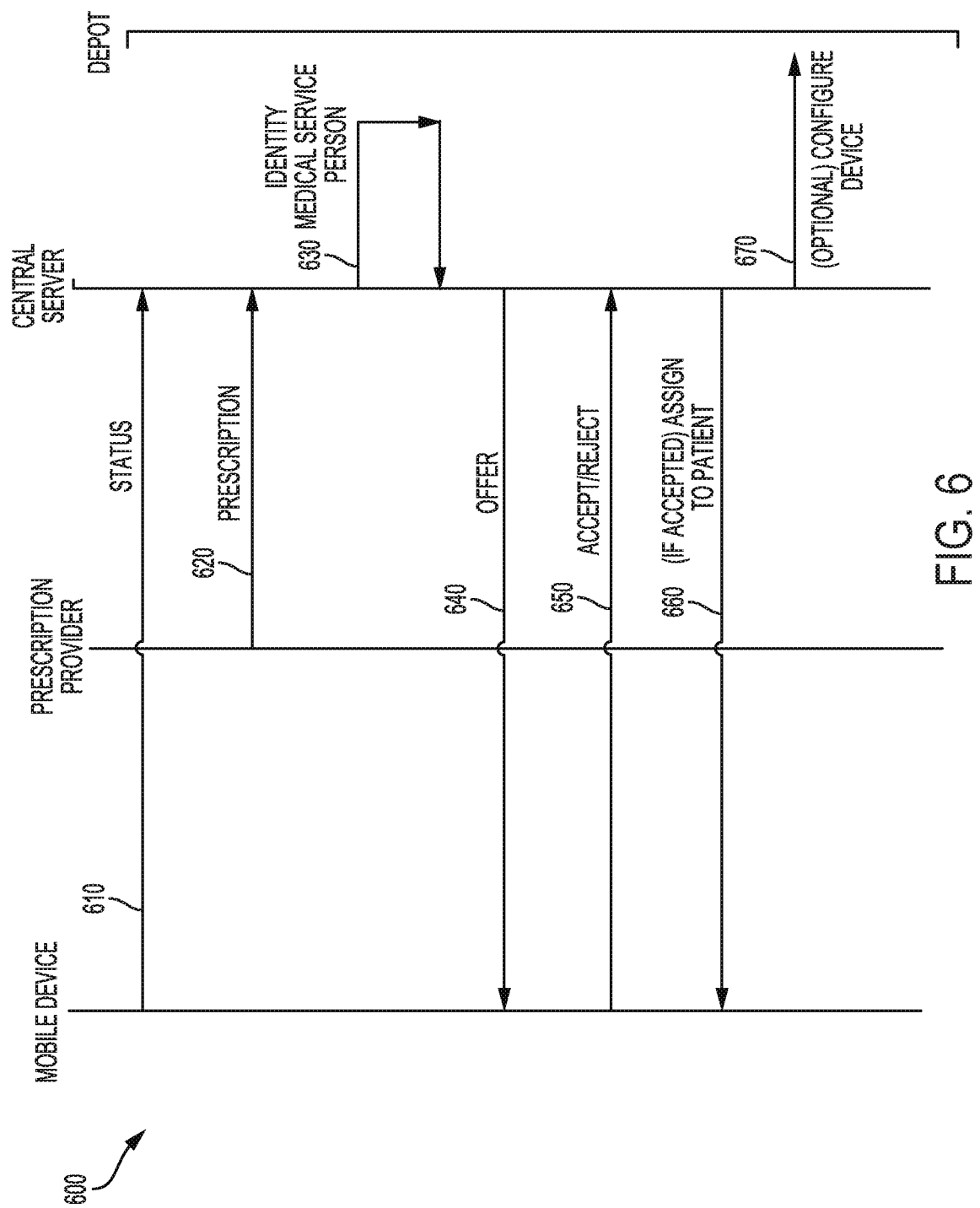
FIG. 6 illustrates an example process for managing medical service personnel.

FIG. 6 shows an example process flow 600 during which a patient is assigned to a medical service person in order to have their prescription fulfilled.

At act 610, the mobile device (e.g., mobile device 560 in FIG. 5) transmits a status of the medical service person (e.g., medical service person 570) to the central server (e.g., central server 550). The medical service person's interactions with the central server, the depot device(s), and other components as described herein may be performed through a mobile application ("app") executed on the mobile device.

The medical service person status information may include, for example, the current location of the medical service person; the schedule and availability of the medical service person; the skills and certifications of the medical service person; and similar information. In some examples, the medical service person status information may include the types of assignments the medical service person is available for. For example, the medical service person may indicate availability for a new patient fitting; for a service call for an existing patient; and/or recovering equipment from an existing patient whose prescription is ending. The medical service person may also indicate availability for tasks having a certain urgency. For example, the medical service person may set a status indicating availability for non-urgent assignments that can be completed within 48-72 hours, but may be unavailable for more urgent assignments.

The medical service person status information may be obtained from the medical service person and/or the mobile device in a number of ways. In one example, the medical service person may be prompted, upon powering up the mobile device or opening the mobile app, to indicate his or her current status. Such status may include, for example, that the medical service person is currently available for new assignments, is not currently available for new assignments, and/or will be available at certain time(s) in the future for new assignments. For example, the app may provide the medical service person with the ability to select date/time ranges (e.g., on a calendar view), or after some duration of time ("in 60 minutes"), during which the app is to automatically set a status of "available" or "unavailable" for the medical service person. At the appropriate times, the app provides the status update to the central server. The app may provide the ability for the medical service person to manually override such an automatic status, such as when the medical service person is unexpectedly unavailable despite an earlier indication of availability.

In some examples, the mobile device may automatically provide the central server with the status of the medical service person in certain circumstances. For example, when the medical service person accepts an assignment, the medical service person's status may be set to unavailable, either for all assignments or for new assignments that conflict with the current assignment in terms of scheduling and location. In another example, if the medical service person closes/shuts down the app and/or powers down the mobile device, the mobile device may be configured to transmit an "unavailable" status to the central server before closing. In another example, the mobile device may be polled periodically (e.g., every 5, 15, or 60 minutes) by the central server. If no response is received one or more times, the central server may automatically set the status of the medical service person to "unavailable." Similarly, the app may periodically provide the central server with a location of the medical service person, as determined by a location detector (e.g., GPS) in the mobile device. The medical service person may be automatically assigned a status of "unavailable" when outside of particular service area or radius, or may be prompted to set their status accordingly.

At act 620, the central server receives a prescription or a new electronic order from an external source (e.g., a medical professional treating the patient). The server can then retrieve one or more prescription parameters from the prescription. The prescription parameters may include such information as the type of equipment to be assigned to the patient; the operating parameters for the equipment for that patient; and other relevant information. The prescription parameters may be sent in a data format such as JSON or XML.

At act 630, the central server receives medical service personnel information and identifies one or more medical service persons as suitable for being assigned the prescription/patient. For example, the medical service personnel information includes information about one or more medical service persons, their availability status, and other information to automatically assess appropriateness for matching with a patient's prescription. The central server may determine the suitability of the medical service person according to a number of predetermined personnel criteria, including the patient's and/or medical service personnel schedule, availability of medical service personnel, location of the patient and/or medical service personnel, assigned territory of the medical service personnel, medical service personnel expertise, medical service personnel certifications, medical service personnel current and/or historic case load, urgency of the assignment, medical service personnel employment status, medical service personnel's prior patient feedback, medical service personnel salary or reimbursement rate, and other factors. For example, the prescription parameters may include information used to determine the suitability of the medical service person needed to fill the prescription. In one hypothetical scenario, the patient may be a 65 year old female, with a history of heart failure complications and in need for a WCD. The patient has had a recent myocardial infarction, currently has atrial fibrillation and is being monitored as a candidate for a possible implanted pacemaker/defibrillator. The patient is not fluent in English, potentially requiring a translator to understand instructions and medical information. In such a scenario, a scheduler or other authorized person may determine that a medical service person with an experience level of 4 or above, with a generally lower current workload (e.g., fewer than 5 patients a week), a high certification (e.g., 5 or higher), located in Chelmsford and has high patient feedback scores may be appropriate.

In some examples, the central server may determine the suitability of the medical service person according to the medical service person's authorization to perform certain assignments, or the medical service person's access rights to one or more depot locations. For example, a medical service person may not be suitably trained or authorized to assign a wearable cardiac device to a new patient and instruct the patient on its use, and so may not be offered such assignments. The same medical service person may be allowed, however, to recover such devices at the end of the prescription. As an example, medical service personnel information that can be used to assign a medical service person to a patient is shown in TABLE 2 below.

TABLE 3

Medical service personnel information

| Name | Gender | Experience level (1-5, 5 most senior) | Current workload | Schedule over 8 hours | Certification (1-6, with 6 highest) | Location | Reimbursement code | Patient feedback score (1-10, 10 most favorable) |
|---|---|---|---|---|---|---|---|---|
| John C. | M | 4 | 4 patients/week | Available | 6 | Chelmsford, MA | 5002 | 8.0 |
| Rob A. | M | 5 | 5 patients/week | Unavailable | 5 | Chelmsford, MA | 4886 | 9.5 |
| Melissa B. | F | 2 | 8 patients/week | Available 2 hours | 4 | Billerica, MA | 5002 | 9.5 |
| Joan C. | F | 1 | 5 patients/week | Unavailable, available in 2 hours | 3 | Chelmsford, MA | 5002 | 8.9 |

In some examples, the central server may identify the most suitable medical service persons, and may selectively offer the assignment to the most suitable first, making the assignment available to others only upon rejection or failure to respond within a certain time period by the selected medical service person. In other examples, the central server may offer the assignment to a larger group, including the entire pool of eligible medical service persons. For example, the server may automatically identify the most suitable medical service person or persons based on a series of configurable rules stored in a memory associated with the central server. For example, the rules may specify based on certain types of fields in the prescription parameters the type of medical service person to be assigned to the patient. If the server is unable to assign a patient after trying a predetermined number of times (e.g., set to a time out threshold of, say, 3 tries), the server may then alert a human scheduler or other authorized person to manual find a medical service person.

At act 640, the offer is transmitted to the mobile device (or other designated device) of the medical service person. The offer may include information such as the location of the medical device equipment and patient, information regarding the prescription, and the like. The offer is presented to the medical service person via a user interface of the mobile device. A mobile app executing on the mobile device may send a push notification alerting the medical service person to the offer. An expiration date/time of the offer, or other conditions of the offer (e.g., first come-first served) may be presented. Other information may also be provided the medical service person, such as where the medical service person interacts with the mobile app to view additional information. Such additional information may include, for example, the current location or treatment location of the patient; the identity of the patient; the type or urgency of the assignment; the depot location at which one or medical devices must be retrieved for the assignment; the pay/reimbursement rate of the assignment. In some examples, the medical service person may be provided the opportunity to request additional information regarding the assignment.

At act 650, the medical service person either accepts or rejects the assignment, with the acceptance or rejection being transmitted by the mobile device to the central server. In examples where the offer is made to a number of medical service persons, the offer may be accepted on a "first come, first served" basis. Once the offer has been accepted by a medical service person, others who have received the offer may be notified that the offer is no longer valid and cannot be accepted. In some examples, the medical service person may be allowed to tentatively accept, or hold, the assignment, for some period of time. If the assignment is not unconditionally accepted within some certain amount of time, or is withdrawn by the central server, then it may be offered to others.

At act 660, if the medical service person has accepted the assignment, the prescription/patient are assigned to the medical service person, and the assignment is confirmed to the medical service person via the mobile device. Additional information about the assignment may also be provided, such as a specific identifier (e.g., serial number) of the equipment to be assigned. In this example, acceptance of the assignment by the medical service person results in a near-instantaneous assignment to the medical service person. The central server 450 and/or a depot device at the location of the equipment to be assigned may notify the medical service person that the assignment has been confirmed, and may provide the medical service person with further information about the assignment.

In some examples, the assignment is selectively awarded to one of a number of accepting medical service persons based on the suitability criteria identified above. For example, the offer may have been initially made to a subset of eligible medical service persons having sufficiently high qualifying criteria (such as current location and current availability). If more than one of those medical service persons indicates a willingness to accept the assignment, then the central server 450 may pick from among those accepting medical service persons based on who is closest to the depot and/or the patient and can provide service the soonest.

At optional step 670, the central server may select a device at an appropriate depot to be assigned to the patient, and may communicate with a depot device at the depot to either configure the device or facilitate a configuration of the device by the medical service person. If the medical device is not immediately assigned to the patient, a hold may be placed on the medical device to avoid a situation in which two patients have been matched to the same medical device.

The app may, based on information received from the central server and/or the depot device, also provide the assigned medical service person with information for locating the device at the depot, and then subsequently locating the patient for the device fitting. For example, the central server may provide information for generating a map of the depot in the app being used by the medical service person, with the particular location of the device being highlighted.

In another example, the depot device may activate a light or other display element near the medical device in the depot upon the arrival of the medical service person, to aid the medical service person in quickly locating the device.

In implementations, the app can also provide active monitoring of the medical service person getting closer to the depot and/or patient. For instance, the app may, using GPS or other location-tracking technology on the mobile device, track the service person's current location relative to the depot and/or the patient's location. This location information can be used for a variety of automated or manual purposes. For example, in a hypothetical scenario, if the medical service person does not follow direction instructions or does not travel to the depot and/or the patient's location within an agreed-on time frame, a scheduler can cause the central server to revoke the medical service person's assignment and re-assign the patient to a different medical service person. In a similar scenario, the central server may be configured with rules stored in an associated memory device to automatically revoke an assignment and re-assign the patient based on certain system violations. A time-stamped and detailed log of all such decisions can be made to the memory device. For example, a rule may be that the service person is to travel to a patient location by 3:00 pm of a certain day. If that time has passed and the service person is deemed based on the service person's location that the patient is not within proximity of the patient (e.g., a configurable value of within 1 mile, 2 miles, or 5 miles, or other predetermined distance), the central server may alert the service person to call a scheduler to provide further information on their status. If no further action is noted, the central server may notify the service person that their assignment has been revoked and transfer the assignment to another service person. Similarly, another rule may be that the service person is to travel to a depot location by 10:00 am of a certain day to pick up medical device equipment for a patient. If that time has passed and the service person is deemed based on the service person's location that the patient is not within proximity of the depot location (e.g., a configurable value of within 1 mile, 2 miles, or 5 miles, or other predetermined distance), the central server may alert the service person to call a scheduler to provide further information on their status. If no further action is noted, the central server may notify the service person that their assignment has been revoked and transfer the assignment to another service person. A similar process can be invoked if the patient is non-compliant and, for example, decides to leave their previously arranged location.

It will be appreciated that while the examples described here involves the assignment of a single patient/prescription for purposes of illustration, the system may allow the medical service person to receive and accept one or more assignments at a time. For example, a medical service person who has already accepted an assignment for a first patient may also accept an assignment for a second patient, subject to any criteria applied relating to scheduling, location, costs, or the like. In some examples, the current case load of assignments being handled by a medical service person may be treated as suitability criteria in determining whether to offer assignments, as discussed above.

Prior to or at the time of assigning and/or delivering the equipment to the patient, the medical service person may use a mobile device to receive equipment inventory information, patient information, and/or prescription parameters, and use that information to assign or configure the device or otherwise facilitate the assignment. The mobile device may also present the medical service person with alerts regarding reports of malfunctioning or expired equipment, equipment to be recovered soon when a prescription ends, etc. The medical service person may also receive detailed or summary reports, either periodically or on demand, regarding patients and/or medical devices or components assigned to them.

Figure 7:
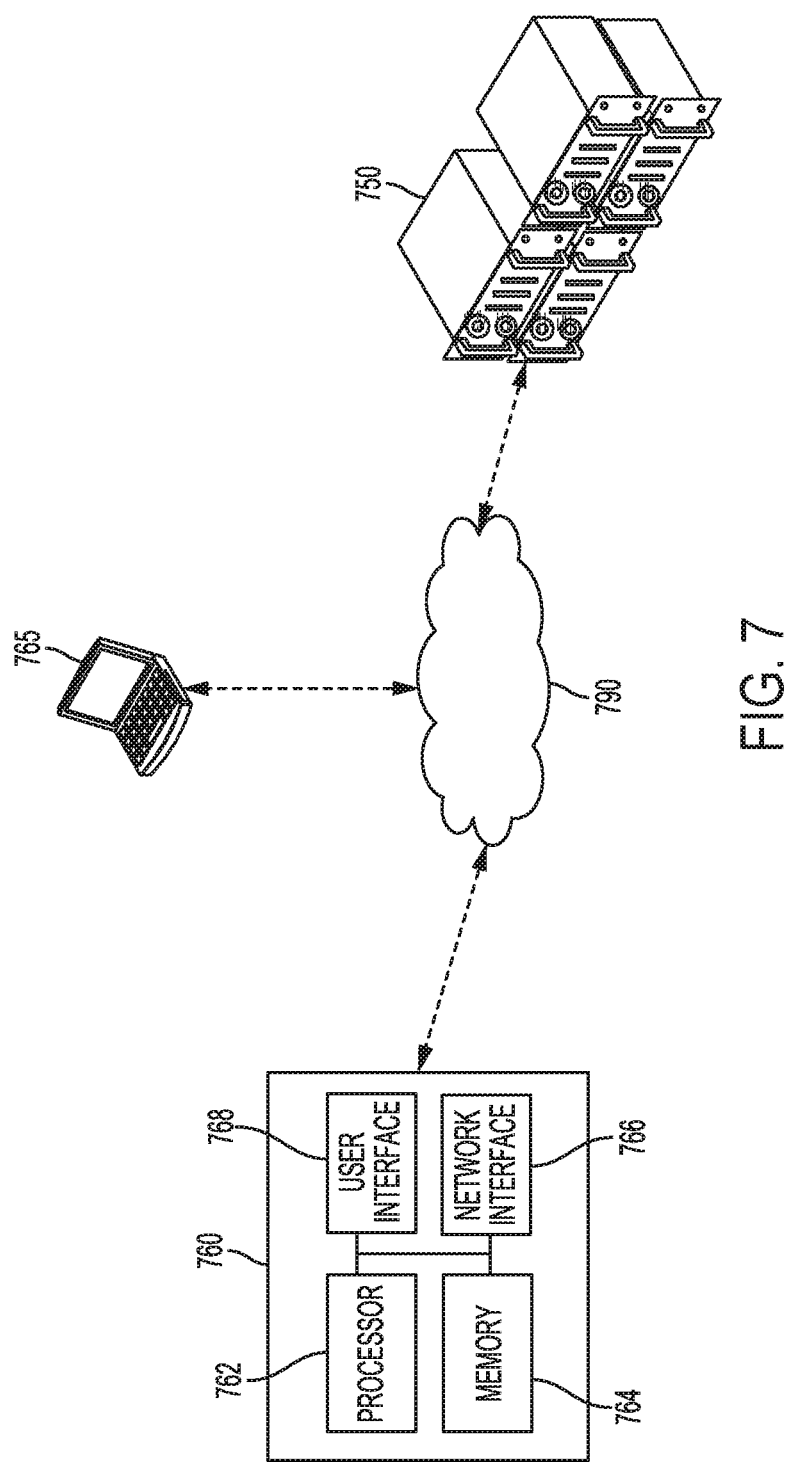
FIG. 7 is a block diagram of an example mobile device architecture and associated system for tracking inventory and managing medical service personnel.

A block diagram of a mobile device 760 (e.g., such as mobile device 560 for use by a medical service person) is shown in FIG. 7. The mobile device 760 is configured to interact with a central server 750 and/or another device 765 via a network 790. The mobile device 760 includes a processor 762, a memory 764, a network interface 766, and a user interface 768. The user interface 768 may be a graphical user interface configured to display one or more interfaces or screens allowing the medical service person to customize and facilitate the assignment, as discussed in more detail below. In implementations, mobile device 760 may also be used by technicians and/or schedulers for managing assignments of medical service persons with patients.

Figure 8:
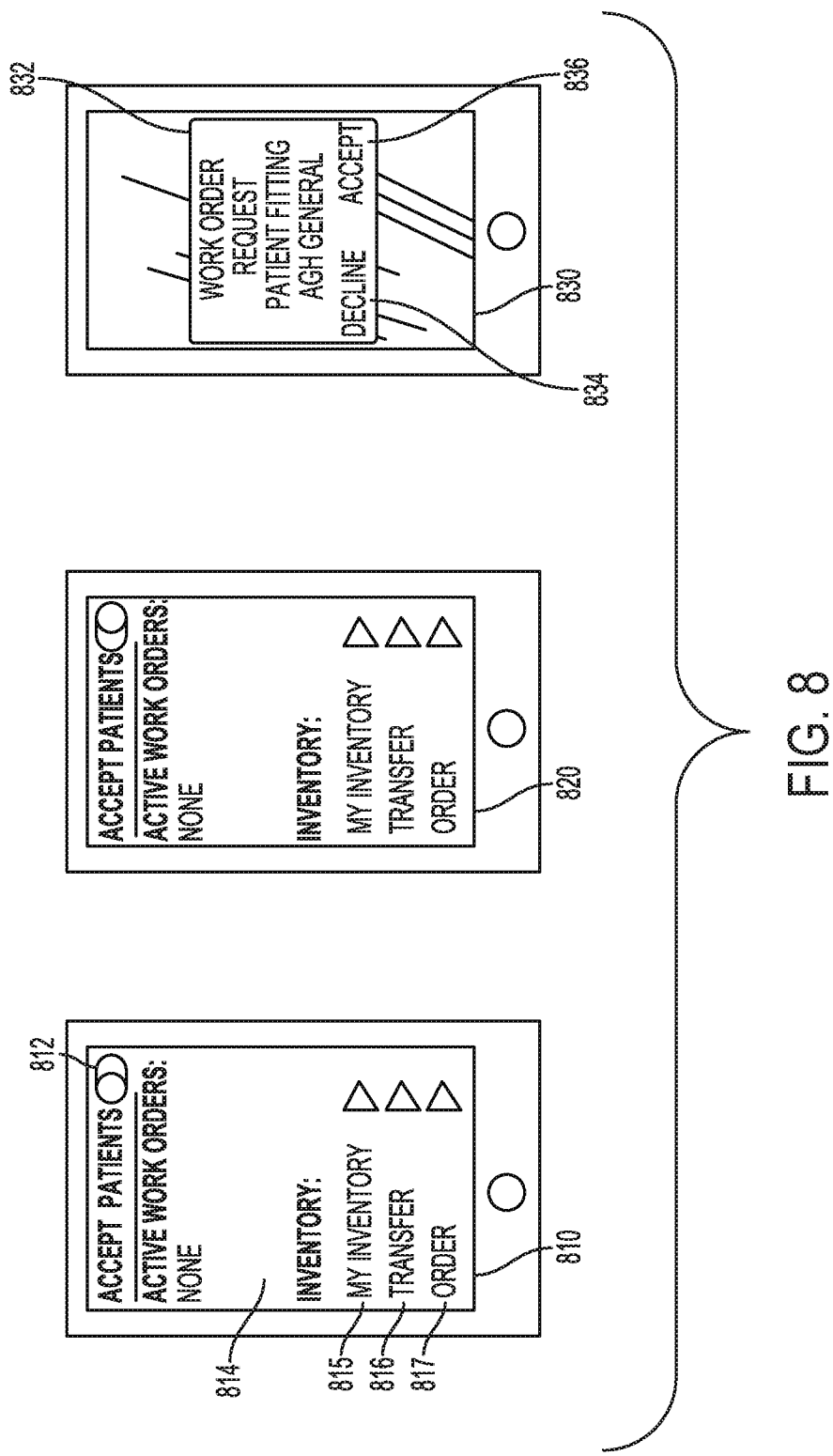
FIG. 8 illustrates example user interfaces for tracking inventory and managing medical service personnel.

FIG. 8 shows an example user interface 810 in which a mobile device of a medical service person (e.g., mobile device 760) has a current state of not accepting patients, as indicated by slider 812 being in the left (OFF) position. The interface 810 also has an active work order field 814 for displaying information about the medical service person's current assignment list or backlog (currently empty). The interface 810 also includes an inventory interface element 815 that can be selected in order to display information about a current inventory accessible or managed by the medical service person at one or more depot locations, as discussed in more detail below. The interface 810 also includes a transfer interface element 816 that can be selected in order to complete a transfer of a medical device and/or components to or from a patient, as discussed in more detail below. The interface 810 also includes an order interface element 817 that can be selected in order to request that a medical device and/or components be assigned to the patient, as discussed in more detail below.

In the interface 820, the slider 812 has been moved to the right (ON) position, either by the medical service person or automatically by the application (e.g., according to a scheduled start time of the medical service person). This updated status of the medical service person is transmitted to the central server, notifying the central server that the medical service person is now accepting assignments for new patients/prescriptions.

In the interface 830, the mobile device has received an offer of an assignment from the central server, and has displayed a message 832 to that effect to the medical service person. The message 832 indicates a type of the assignment ("Patient Fitting"), a location of the patient ("AGH General"), and possibly other information. Interface elements 834 and 836 allow the medical service person to either decline or accept the assignment, respectively. If the medical service person accepts the assignment, then the patient may be assigned to the medical service person as discussed herein.

Figure 9:
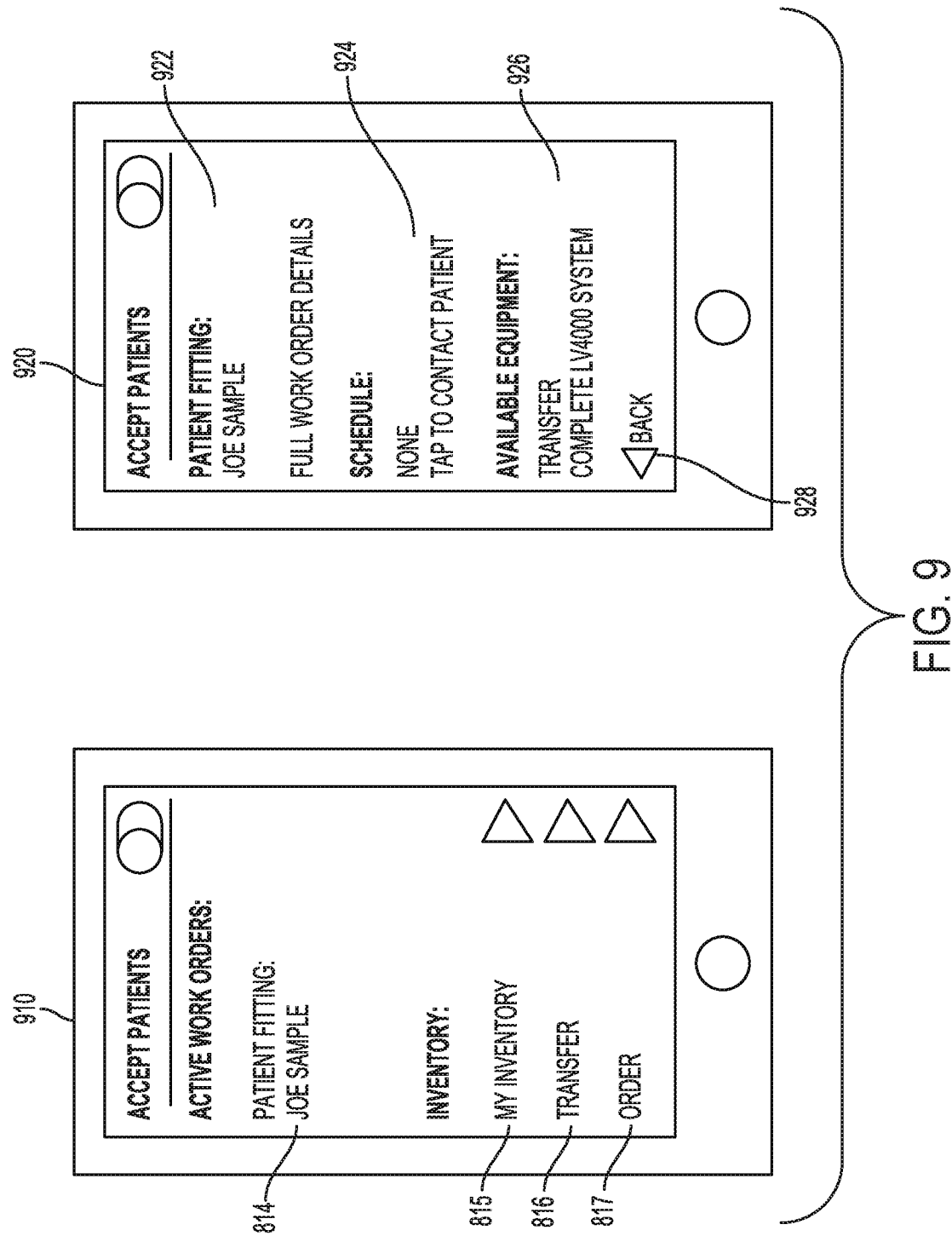
FIG. 9 illustrates example user interfaces for tracking inventory and managing medical service personnel.

In addition to allowing the medical service person to receive, review and accept or reject assignments, the mobile device may provide interfaces that allow the medical service person to perform or access information about the assignment. In the interface 910 shown in FIG. 9, the medical service person is presented with various options discussed above with respect to interface 810. Now that the medical service person has accepted the assignment (as discussed with reference to FIG. 8), information about the assignment can be viewed by interacting with work order field 814; as can be seen, a work order for a "Patient Fitting" for "Joe Sample" can be accessed, for example, by clicking on the work order in the list.

Interface 920 is displayed when the medical service person opens the work order for "Joe Sample." In particular, the interface 920 includes a patient fitting field 922 that the medical service person can interact with to view full work order details; a schedule field 924 that the medical service person can interact with to schedule an appointment with or contact the patient; an equipment field 926 that the medical service person can interact with to assign equipment to or from a patient; and a back button 928 that returns to interface 910.

Figure 10:
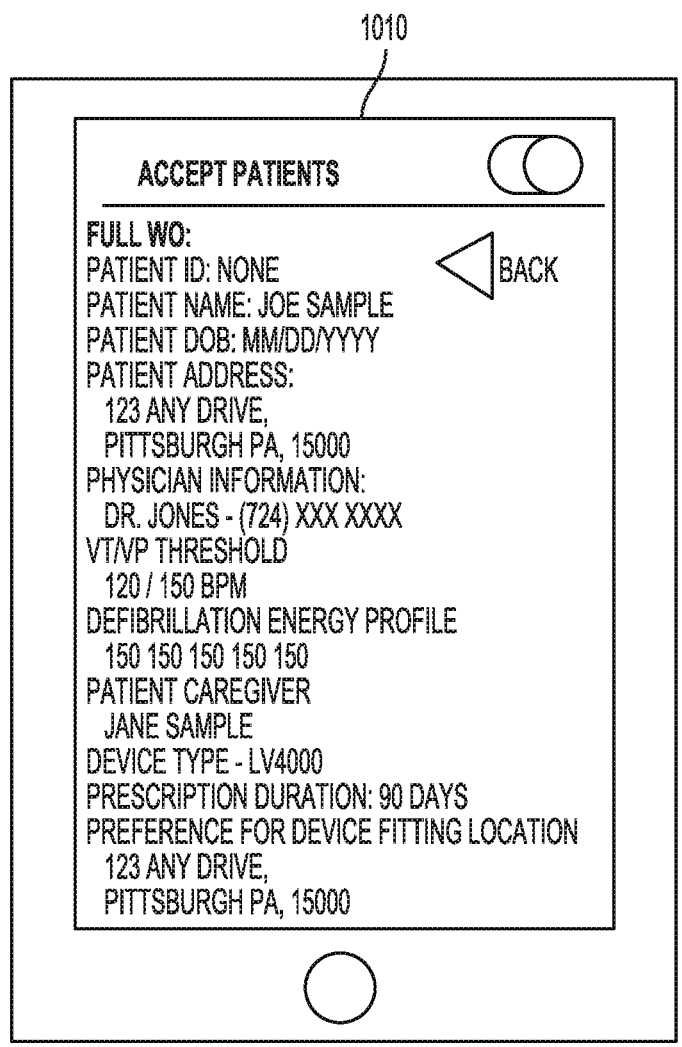
FIG. 10 illustrates an example user interface for tracking inventory and managing medical service personnel.

If the medical service person interacts with the patient fitting field 922, an interface 1010 may be shown as seen in FIG. 10. The interface 1010 may display detailed information regarding the patient, the prescription, and/or any devices or components associated with the patient. For example, the interface 1010 may display information regarding the patient's name, patient identifier, patient date of birth, patient address, and information about the patient's physician and/or caregiver. The interface 1010 may also include information relating to the patient's condition and/or parameters to be applied by an assigned device in monitoring or treating the condition, including threshold information relating to the patient's condition (e.g., VT/VF threshold for a cardiac patient), a defibrillation energy profile, a device type to be assigned to the patient, a prescription duration, and a preferred location for interacting (e.g., participating in a fitting of a medical device) with the medical service person, such as at the patient's home or in the hospital.

Figure 11:
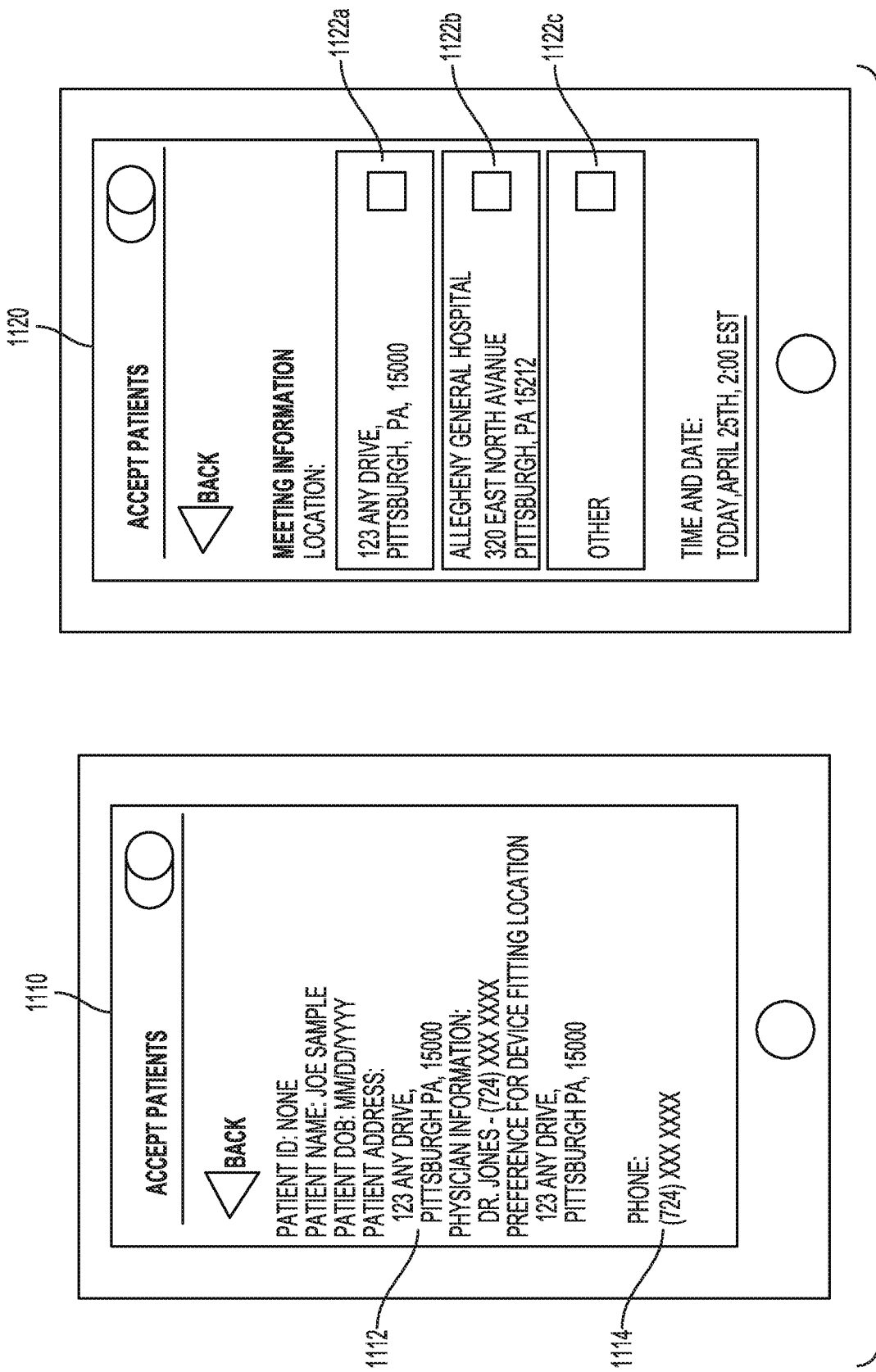
FIG. 11 illustrates example user interfaces for tracking inventory and managing medical service personnel.

Returning to FIG. 9, if the medical service person interacts with the schedule field 924 in interface 920, an interface providing information for contacting the patient may be displayed. Such an interface 1110 can be seen in FIG. 11. The interface 1110 displays information 1112 including a patient identifier, patient name, patient date of birth, patient address, physician information, and a preferred location for interacting with the medical service person. In some examples, the interface 1110 may provide functionality for allowing the medical service person to contact the patient or (or caregiver for the patient) from within the interface 1110. For example, the interface 1110 may provide an interface element 1114 allowing the medical service person to dial the patient's phone number and be connected to the patient by phone, or to email, text message, or video chat with the patient.

In some examples, the medical service person may be provided with navigation instructions to meet with the patient at one or more locations. For example, in the interface 1120 shown in FIG. 11, the medical service person may be provided the opportunity to select from among several addresses 1122a-c associated with the patient, and to be provided instructions, maps, and/or turn/by turn navigation steps to that location. In some examples, the medical service person may be provided the option to send an estimated time of arrival to the patient, or to share the medical service person's current location with the patient.

Figure 12:
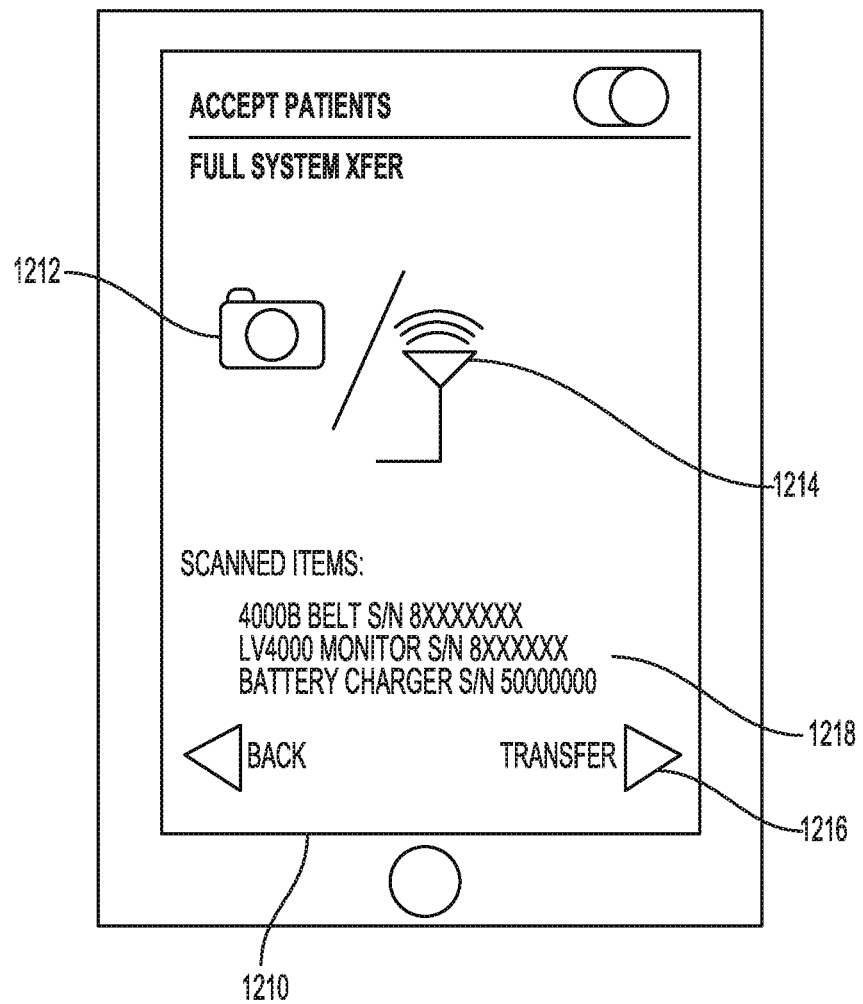
FIG. 12 illustrates an example user interface for tracking inventory and managing medical service personnel.

The medical service person may also be provided with an interface 1210 allowing for the transfer of a medical device or component to the patient, as seen in FIG. 12. The interface 1210 may allow the medical service person to identify medical devices or components to be transferred, such as by optically scanning a label with a camera (using camera icon 1212) or by reading an RFID signal from a tag on the device or component (using tag icon 1214). Once the component(s) to be transferred to the patient have been identified, they may be displayed in the interface 1210 in item field 1218. In other examples, devices or components to be transferred to the patient may be identified automatically by the application, by a central server or depot device, or by another person interacting with any of those components. In order to transfer the identified assets to the patient, the medical service person may interact with a transfer button 1216. To complete the transfer, the mobile device transmits information about the assignment to the central server, which updates inventory records accordingly. For example, the central server may store an indication in the inventory records associating the medical device with the patient and/or the medical service person. In some examples, the inventory assigned to patients by a medical service person may be associated with the medical service person, in order to track what inventory that medical service person is responsible for in the field. The central server may also send a notification of the assignment to other entities, including the patient, the patient's medical or personal caregiver, the person's insurance company, or the like.

Figure 12A:
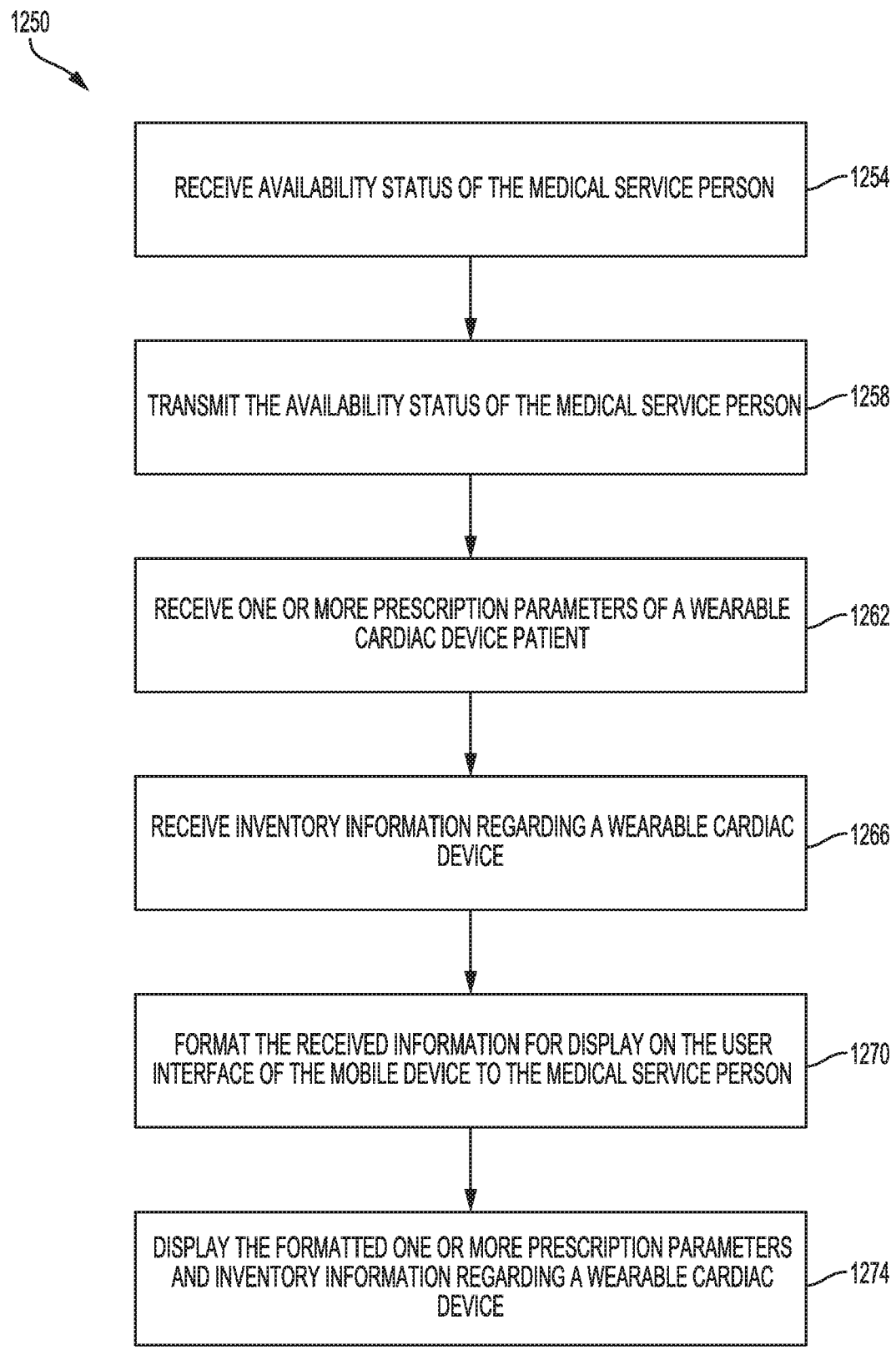
FIG. 12A illustrates an example process implemented by a mobile device associated with a medical service person.

FIG. 12A shows an exemplary process 1250 implemented by a mobile device associated with a medical service person. In this exemplary process, the mobile device receives (e.g., from a graphical user interface) a status of a medical service person; transmits that status (e.g., to the central server); receives one or more prescription parameters for a wearable cardiac device to be assigned to a patient; receives inventory information for a wearable cardiac device and associated components, all of which are identified for the patient based on the prescription parameters; and formats and displays the prescription parameters and the inventory information on the graphical user interface.

At step 1254, the mobile device receives from a medical service person, via a graphical user interface of the mobile device, an availability status of the medical service person to indicate if the medical service person is available to accept new prescriptions. For example, the mobile device may prompt the medical service person periodically to indicate whether the medical service person is available to accept new prescriptions. In another example, the medical service person may be prompted to indicate their availability upon completion of a previous assignment. In addition to current availability, the medical service person may be prompted to indicate their availability schedule for the next several hours, day, week, or month. In addition to prompting the user via the graphical user interface, the mobile device may employ other interfaces, such as tactile (e.g., vibrate) or audio (e.g., audible alert) to elicit the medical service person's availability.

The medical service person status information may include, for example, the current location of the medical service person; the schedule and availability of the medical service person; the skills and certifications of the medical service person; and similar information. In some examples, the medical service person status information may include the types of assignments the medical service person is available for. For example, the medical service person may indicate availability for a new patient fitting; for a service call for an existing patient; and/or recovering equipment from an existing patient whose prescription is ending. The medical service person may also indicate availability for tasks having a certain urgency. For example, the medical service person may set a status indicating availability for non-urgent assignments that can be completed within 48-72 hours, but may be unavailable for more urgent assignments.

The medical service person status information may be obtained from the medical service person and/or the mobile device in a number of ways. In one example, the medical service person may be prompted, upon powering up the mobile device or opening the mobile app, to indicate his or her current status. Such status may include, for example, that the medical service person is currently available for new assignments, is not currently available for new assignments, and/or will be available at certain time(s) in the future for new assignments. For example, the app may provide the medical service person with the ability to select date/time ranges (e.g., on a calendar view), or after some duration of time ("in 60 minutes"), during which the app is to automatically set a status of "available" or "unavailable" for the medical service person. At the appropriate times, the app provides the status update to the central server. The app may provide the ability for the medical service person to manually override such an automatic status, such as when the medical service person is unexpectedly unavailable despite an earlier indication of availability.

In some examples, the mobile device may automatically provide the central server with the status of the medical service person in certain circumstances. For example, when the medical service person accepts an assignment, the medical service person's status may be set to unavailable, either for all assignments or for new assignments that conflict with the current assignment in terms of scheduling and location. In another example, if the medical service person closes/shuts down the app and/or powers down the mobile device, the mobile device may be configured to transmit an "unavailable" status to the central server before closing. In another example, the mobile device may be polled periodically (e.g., every 5, 15, or 60 minutes) by the central server. If no response is received one or more times, the central server may automatically set the status of the medical service person to "unavailable." Similarly, the app may periodically provide the central server with a location of the medical service person, as determined by a location detector (e.g., GPS) in the mobile device. The medical service person may be automatically assigned a status of "unavailable" when outside of particular service area or radius, or may be prompted to set their status accordingly.

At step 1258, the mobile device transmits the availability status of the medical service person associated with the mobile device. For example, the availability status of the medical service person may be sent to the central server. In some examples, the availability status may be encapsulated in a format such as JSON or XML. In one example, the medical service person's current availability status is transmitted as a binary value, e.g., "available" or "not available." In another example, the medical service person's availability schedule is transmitted in a format expected by the recipient, such as with an availability status for one or more time spans.

At step 1262, the mobile device receives, via the network interface of the mobile device, one or more prescription parameters of a wearable cardiac device patient based on a prescription received at a central server and in response to the transmitted availability status of the medical service person. In some examples, the prescription parameters relate to the operation of a wearable cardiac device to be worn by a patient for some period of time. The prescription parameters may be passed to the mobile device in a format such as JSON or XML, and may include the types of parameters discussed above, including a type of the medical device, the patient's underlying medical condition, the patient's age, gender, and other identifying characteristics and biometric information, a duration of wear of the medical device, monitoring and/or treatment settings for the device, the patient's size and fit (e.g., for garment(s) to be worn with the device), the location of the patient, and the patient's personal preferences, if any.

At step 1266, the mobile device receives, via a network interface of the mobile device, inventory information regarding a wearable cardiac device and associated plurality of separate wearable cardiac device components that is identified for the wearable cardiac device patient based on the one or more prescription parameters. The inventory information may include the types of inventory information discussed above, including identifiers of individual components (e.g., serial or inventory number), as well as their type (e.g., defibrillator), make, model, size, location within the depot (e.g., aisle, shelf, rack, etc. designated by a predetermined reference scheme), version (e.g., firmware version), expiration date, next service date, and deployment status. The mobile device may receive the information in a transmission format, such as JSON or XML, and re-format the inventory information to be stored in a memory on the mobile device. For example, the inventory information may be stored in a relational database.

At step 1270, the mobile device formats the received one or more prescription parameters and inventory information regarding a wearable cardiac device and associated plurality of separate wearable cardiac device components that is identified for the wearable cardiac device for display on the user interface of the mobile device to the medical service person. For example, only prescription information and/or inventory information relevant to a current prescription being handled by the medical service person may be formatted for display. In another example, only those information fields relevant to a current task of the medical service person may be formatted for display. For instance, if the medical service person has elected to view relevant inventory at a particular depot location, the location of each device need not be separately displayed.

At step 1274, the mobile device displays, on the graphical user interface of the mobile device, the formatted one or more prescription parameters and inventory information regarding a wearable cardiac device and associated plurality of separate wearable cardiac device components.

Example Case Studies

A few example case studies will now be described.

Figure 14:
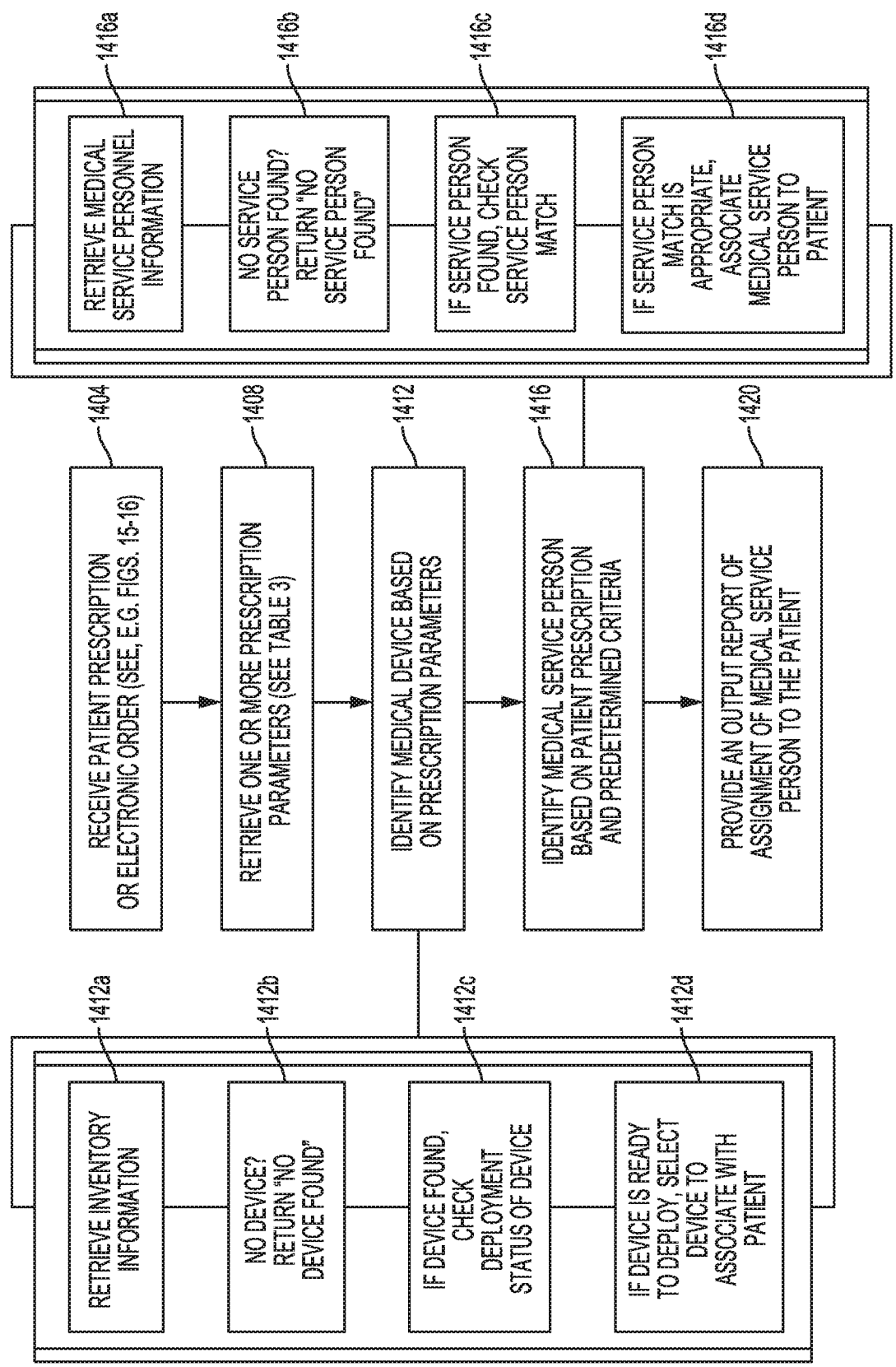
FIG. 14 is an example process for tracking and managing prescription, inventory and medical service personnel.

In a first example case study, a patient has been prescribed a wearable defibrillator device to be worn substantially continuously for 30 days. For example, an automated process 1400 as shown in FIG. 14 may be carried out on a central server, one or more depot servers, or a combination of the central server and one or more depot servers. Alternatively, process 1400 may be carried out on a tablet, a handheld device, or other mobile software platform. In some implementations, one or a plurality of the steps of process 1400 may be executed by one or more of the central server, a tablet or handheld device, and one or more depot servers.

For example, the process 1400 begins on receiving the patient prescription or electronic order in step 1404. In some implementations, the patient prescription may be provided to the process via an electronic ordering process. For example, a sample prescription order for a treatment device is shown in FIG. 15. A sample prescription order for a patient monitoring device is shown in FIG. 16. For the patient in this case study, the prescription is for a wearable defibrillator, a treatment device, and may be entered via the interface of FIG. 15. The prescription or electronic order interface may be implemented for use at a physician's office.

Accordingly, a physician or a physician's assistant may access the prescription or electronic order interface using preassigned security credentials. Alternatively or in addition, the prescription interface may be available at a central location for use by a technician at direction from a prescribing physician. As shown, the prescription can include the prescribing physician information 1504, 1604, and the patient's biographical information 1508, 1608. In some examples, the prescription can include an estimated length of need of the device 1512, 1612, in this case, 30 days. Further, the prescription can specify device configuration setting information 1516, 1616. Optionally, the prescription or electronic order may include patient insurance information 1510, 1610.

In the foregoing case, the patient prescription may include details as shown in TABLE 3 below. In step 1408, the server can retrieve the prescription details or parameters and store this information in a database.

TABLE 4

| Prescription details or parameters |
| --- |
| Male, 42 inches, arm length 44 inches |
| WCD prescription, VT threshold 150 beats per minute, 5 pulses defibrillation, 125 joules, escalating |
| Monitor for other cardiac conditions |
| Needs fluid monitoring |
| Cardiac rehabilitation routine recommended; periodic WalkTest ™ assessments |
| Request periodic health status information |

As noted, the patient is a male patient, with physical characteristics of vest size 42 inches, and arm length 44 inches. The patient is being prescribed a wearable defibrillator. The prescription indicates that the VT threshold is to be set at 150 beats per minute, 5 pulses of potential defibrillation energy, with the first pulse at 125 joules, and subsequent pulses escalating in 10 joule increments. The wearable defibrillator monitors for other cardiac conditions (such as atrial fibrillation). In addition, the patient is in need for thoracic fluid monitoring, and further, one or more cardiac rehabilitation routines (e.g., device supervised exercise or walking activity) is recommended. In addition, the patient is being prescribed to have periodic WalkTest™ assessments, as well as health check-ins.

In step 1412, on receiving the prescription parameters, the process 1500 can automatically identify a suitable wearable defibrillator for the patient. The process 1400 invokes a subprocess 1412a-d. In step 1412a, the server retrieves inventory information to determine whether there is a medical device that can be used to fulfil the patient's prescription for a wearable medical device. Here, the device can include a WCD monitor (e.g., monitor 20 as shown in FIG. 1A), a battery charger (item 40 in FIG. 1A), and a holster (item 30 in FIG. 1A). In step 1412b, if no device can be found in inventory, the subprocess 1412a-d can return a message that no suitable device was found for the patient's prescription. In this case, the process 1500 can pause to provide information to the user that no device was identified, and whether the user would like to add a new device to the inventory. In step 1412c, if a device is found in inventory, subprocess 1412a-d can determine a deployment status of the device, including whether the device has been recently refurbished, whether the device has completed a maintenance protocol, and whether the WCD monitor batteries have been fully charged. In step 1412d, the selected WCD monitor and associated components is then associated with the patient.

In step 1416, the process 1400 invokes the medical service person subprocess 1416a-d. In step 1416a, the subprocess 1416a-d retrieves medical service person information to determine whether there is a suitable medical service person that can be matched to the patient based on the patient's prescription for a wearable medical device. In step 1416b, if no medical service person is found, e.g., there is not at least one medical service person in a local geographical region of the patient who is available to take on a new patient, then the subroutine 1416a-d can return a message to the main process 1400 indicating that no service person was found. In this case, the process 1500 can pause to provide information to the user that no service person was identified, and whether the user would like to add a new medical service person to the system or take other action. In step 1416c, if a medical service person is found, subprocess 1416a-d can determine whether the medical service person is an appropriate match for the patient (see examples provides in connection with FIG. 6 above).

In step 1416d, the selected medical service person is associated with the patient. The medical service person can then travel to either the depot, the patient's location, or a caregiver's office and outfit the patient with the selected medical device. For example, the selected medical device can be shipped to the patient's location or the caregiver's office. In step 1420, an output report can be provided indicating assignment of the identified medical service person to the patient. For example, the output report can be provided as via a display or user interface of a technician computer connected to the central server (e.g., server 350). For example, the output report may be provided as a printed or electronic document (e.g., in portable document format or PDF) to the technician for further use in the technician's work. In some implementations, the output report may be displayed on a portable device, such as a smartphone or a tablet for viewing by the technician or the medical service person. In implementations, the output report can include audible output features, such as, an audible message communicating the assignment of the medical service person to the patient.

In another scenario, the medical service person receives a phone call from a patient who has depleted the supply of electrode gel initially provided by the medical service person at the start of the prescription. In response, the medical service person can use the mobile app to cause replacement gel packets, whose location is tracked by a depot device using, for example, RFID, to be automatically sent to the patient. By communicating with the depot device, the mobile device can identify the replacement packs and assign them to the patient (e.g., using interface 1210 as shown in FIG. 12).

In one scenario, the medical service person may receive a notification that a patient's prescription for a wearable cardiac device is about to end. Accordingly, the medical service person can use the mobile app to schedule a time with the patient (e.g., by sending a SMS message) to retrieve the device. Alternatively, the patient may be automatically notified (e.g., via a message on a user interface of the device, such as display 21 of monitor 20 of FIG. 1) to prepare the device for return to the depot. Upon recovering the device, the personnel at the depot or the medical service person may note that the monitor of the device has suffered some minor physical damage. The depot person or medical service person (using the mobile app) can flag the device to be serviced, meaning it must be repaired and refurbished appropriately before being assigned to another patient.

In another example use case, the central server may automatically notify a medical service person that the battery of a medical device assigned to a patient is not holding a charge for a sufficient time. Such a notification may originate from the device itself, which may send an alert and any available diagnostic information to the central server when the device is charging and/or in communication with a hotspot. Such notifications may be sent automatically, or the medical service person may be given permission by the patient to request and be provided with battery and other status information from the medical device periodically.

In another example use case, the central server may determine that a medical service person who has been given an assignment to fit a patient with a wearable cardiac monitor has not handled such an assignment for some amount of time (e.g., 6 months), or has gone some amount of time without receiving periodic training on such assignments. The medical service person may be required to complete a training module on the mobile device prior to being awarded the assignment. As another example, the medical service person may be instructed to provide the patient with access to a training module (such as on the patient's computer, or on the medical service person's mobile device) as part of the initial assignment of the medical device to the patient.

Example Medical Devices

As described above, the teachings of the present disclosure can be generally applied to inventorying, tracking, transferring, or prescribing external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device can be capable of continuous use by the patient. In some implementations, the continuous use can be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., electrocardiogram (ECG) information, including arrhythmia information, heart vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, lung vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In some implementations, the medical device may be a patient monitoring device with no treatment or therapy functions. For example, such a patient monitoring device can include a cardiac monitoring device or a cardiac monitor that is configured to monitor one or more cardiac physiological parameters of a patient, e.g., for remotely monitoring and/or diagnosing a condition of the patient. For example, such cardiac physiological parameters may include a patient's ECG information, heart vibrations (e.g., using accelerometers or microphones), and other related cardiac information. A cardiac monitoring device is a portable device that the patient can carry around as he or she goes about their daily routine. The cardiac monitor may be configured to detect the patient's ECG through a plurality of cardiac sensing electrodes. For example, a cardiac monitor may be attached to a patient via at least three adhesive cardiac sensing electrodes disposed about the patient's torso. Such cardiac monitors are used in mobile cardiac telemetry (MCT) and/or continuous cardiac event monitoring applications, e.g., in patient populations reporting irregular cardiac symptoms and/or conditions. Example cardiac conditions can include atrial fibrillation, bradycardia, tachycardia, atrioventricular block, Lown-Ganong-Levine syndrome, atrial flutter, sinoatrial node dysfunction, cerebral ischemia, syncope, atrial pause, and/or heart palpitations. For example, such patients may be prescribed a cardiac monitor for an extended period of time, e.g., 10 to 30 days, or more. In some mobile cardiac telemetry applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, heart vibrations (e.g., using accelerometers or microphones), lung vibrations, breath vibrations, sleep related parameters (e.g., snoring, sleep apnea), tissue fluids, among others.

Figure 13:
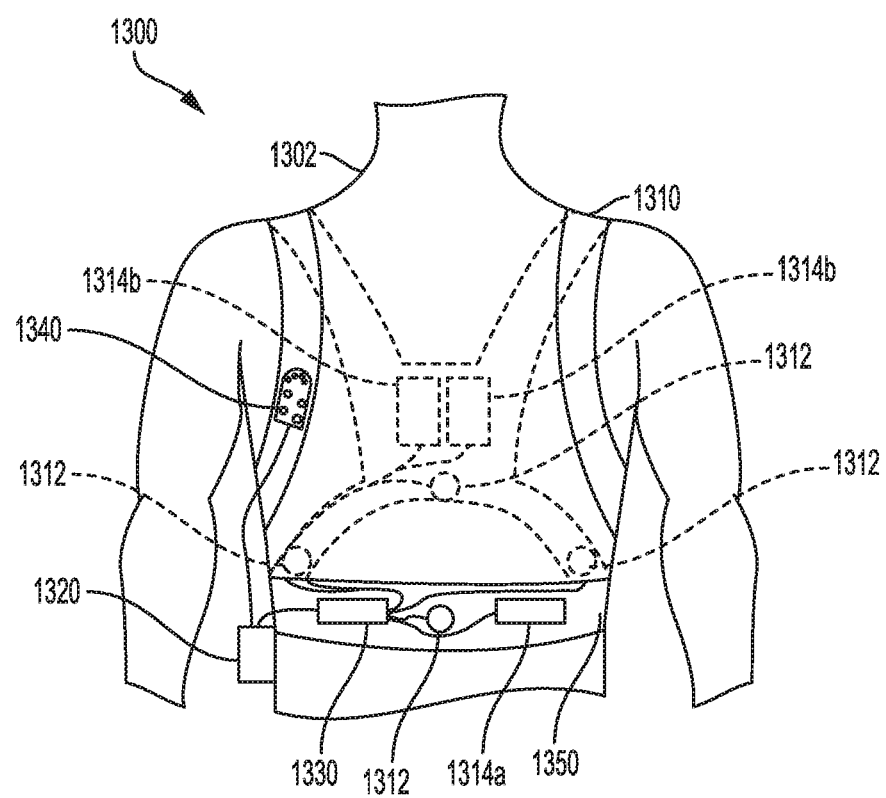
FIG. 13 is an illustration of one example of a wearable medical device.

FIG. 13 illustrates an example medical device 1300 that is external, ambulatory, and wearable by a patient 1302, and configured to implement one or more configurations described herein. For example, the medical device 1300 can be a non-invasive medical device configured to be located substantially external to the patient. Such a medical device 1300 can be, for example, an ambulatory medical device that is capable of and designed for moving with the patient as the patient goes about his or her daily routine. For example, the medical device 1300 as described herein can be bodily-attached to the patient such as the LifeVest® wearable cardioverter defibrillator available from ZOLL® Medical Corporation. In one example scenario, such wearable defibrillators can be worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 1300 can include one or more of the following: a garment 1310, one or more sensing electrodes 1312 (e.g., ECG electrodes), one or more therapy electrodes 1314a and 1314b (collectively referred to herein as therapy electrodes 1314), a medical device controller 1320, a connection pod 1330, a patient interface pod 1340, a belt 1350, or any combination of these. In some examples, at least some of the components of the medical device 1300 can be configured to be affixed to the garment 1310 (or in some examples, permanently integrated into the garment 1310), which can be worn about the patient's torso.

The medical device controller 1320 can be operatively coupled to the sensing electrodes 1312, which can be affixed to the garment 1310, e.g., assembled into the garment 1310 or removably attached to the garment, e.g., using hook and loop fasteners. In some implementations, the sensing electrodes 1312 can be permanently integrated into the garment 1310. The medical device controller 1320 can be operatively coupled to the therapy electrodes 1314. For example, the therapy electrodes 1314 can also be assembled into the garment 1310, or, in some implementations, the therapy electrodes 1314 can be permanently integrated into the garment 1310.

Component configurations other than those shown in FIG. 13 are possible. For example, the sensing electrodes 1312 can be configured to be attached at various positions about the body of the patient 1302. The sensing electrodes 1312 can be operatively coupled to the medical device controller 1320 through the connection pod 1330. In some implementations, the sensing electrodes 1312 can be adhesively attached to the patient 1302. In some implementations, the sensing electrodes 1312 and at least one of the therapy electrodes 1314 can be included on a single integrated patch and adhesively applied to the patient's body.

The sensing electrodes 1312 can be configured to detect one or more cardiac signals. Examples of such signals include ECG signals and/or other sensed cardiac physiological signals from the patient. In certain implementations, the sensing electrodes 1312 can include additional components such as accelerometers, acoustic signal detecting devices, and other measuring devices for recording additional parameters. For example, the sensing electrodes 1312 can also be configured to detect other types of patient physiological parameters and acoustic signals, such as tissue fluid levels, heart vibrations, lung vibrations, respiration vibrations, patient movement, etc. Example sensing electrodes 1312 include a metal electrode with an oxide coating such as tantalum pentoxide electrodes, as described in, for example, U.S. Pat. No. 6,253,099 entitled "Cardiac Monitoring Electrode Apparatus and Method," the content of which is incorporate herein by reference.

In some examples, the therapy electrodes 1314 can also be configured to include sensors configured to detect ECG signals as well as other physiological signals of the patient. The connection pod 1330 can, in some examples, include a signal processor configured to amplify, filter, and digitize these cardiac signals prior to transmitting the cardiac signals to the medical device controller 1320. One or more of the therapy electrodes 1314 can be configured to deliver one or more therapeutic defibrillating shocks to the body of the patient 1302 when the medical device 1300 determines that such treatment is warranted based on the signals detected by the sensing electrodes 1312 and processed by the medical device controller 1320. Example therapy electrodes 1314 can include conductive metal electrodes such as stainless-steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1314 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

The invention claimed is:

1. An inventory management system for wearable cardiac devices, the inventory management system comprising:
   a plurality of separate wearable cardiac device components stored as inventory at a first inventory location, the plurality of separate wearable cardiac device components configured to form one of an operable wearable cardiac monitoring device or an operable wearable cardiac monitoring and treatment device;
   a plurality of communication interface circuits associated with a corresponding one of the plurality of separate wearable cardiac device components and configured to facilitate transmission of inventory information through a network;
   at least one server device disposed at a central location and communicatively coupled to the network, the at least one server device comprising
      a processor, and
      a memory communicatively coupled to the processor and comprising instructions that when executed by the processor cause the processor to
         receive the inventory information from the plurality of communication interface circuits via the network;
         receive a prescription for a patient;
         retrieve one or more prescription parameters based on the prescription for the patient;
         locate, in the inventory information, an associated plurality of separate wearable cardiac device components to form the one of the operable wearable cardiac monitoring device or the operable wearable cardiac monitoring and treatment device and that fulfills the prescription parameters;
         determine a deployment status of the associated plurality of separate wearable cardiac device components;
         select the one of the operable wearable cardiac monitoring device or the operable wearable cardiac monitoring and treatment device for the patient including the associated plurality of the separate wearable cardiac device components on determining that the deployment status indicates that the associated plurality of separate wearable cardiac device components is ready to be deployed to the patient; and
         configure the one of the operable wearable cardiac monitoring device or the operable wearable cardiac monitoring and treatment device for the patient including the associated plurality of the separate wearable cardiac device components according to the prescription for the patient.

2. The inventory management system of claim 1, wherein the memory further comprises instructions that when executed by the processor cause the processor to automatically configure the one of the operable wearable cardiac monitoring device or the operable wearable cardiac monitoring and treatment device according to the one or more prescription parameters.

3. The inventory management system of claim 1, wherein the memory further comprises instructions that when executed by the processor cause the processor to display a user interface configured to allow a user to configure the one of the operable wearable cardiac monitoring device or the operable wearable cardiac monitoring and treatment device.

4. The inventory management system of claim 1, wherein the one of the operable wearable cardiac monitoring device or the operable wearable cardiac monitoring and treatment device is a wearable defibrillator, and wherein the one or more prescription parameters comprises one or more treatment parameters for delivering therapy to treat a cardiac condition of the patient via the wearable defibrillator.

5. The inventory management system of claim 4, wherein the one or more treatment parameters includes at least one of a treatment energy level, a pulse count, a pulse duration, and a pulse frequency.

6. The inventory management system of claim 1, wherein the at least one server device is a first server device at the central location, the inventory management system further comprising at least one second server device disposed at the first inventory location and communicatively coupled to the network, the at least one second server device configured to:
receive, from the plurality of communication interface circuits, inventory information about at least one component of the plurality of separate wearable cardiac device components at the first location; and
communicate, via the network, the inventory information to the at least one first server device at the central location.

7. The inventory management system of claim 6, wherein the inventory information includes at least one of an identifier of the at least one component, a type of the at least one component, a quantity of the at least one component, a status of the at least one component, a location of the at least one component within a depot, and an expiration date of the at least one component.

8. The inventory management system of claim 1, wherein the prescription includes at least one of a directive to monitor the patient, a directive to monitor and treat the patient, an identity of the patient, a medical condition of the patient, a harness measurement of the patient, and an operating parameter of the wearable cardiac device.

9. The inventory management system of claim 1, wherein the memory further comprises instructions that when executed by the processor cause the processor to identify a medical service person to fulfill the prescription for the patient based on predetermined medical service person criteria, a status of the medical service person, and the prescription.

10. An inventory management server device at a central location and coupled to a network comprising:
a processor, and
a memory communicatively coupled to the processor and comprising instructions that when executed by the processor cause the processor to receive, via the network, inventory information from a plurality of communication interface circuits regarding a plurality of separate wearable cardiac device components stored as inventory at a first inventory location, the plurality of separate wearable cardiac device components configured to form one of an operable wearable cardiac monitoring device or an operable wearable cardiac monitoring and treatment device;
receive a prescription for a patient;
retrieve one or more prescription parameters based on the prescription for the patient;
locate, in the inventory information, an associated plurality of separate wearable cardiac device components to form the one of the operable wearable cardiac monitoring device or the operable wearable cardiac monitoring and treatment device and that fulfills the prescription parameters;
determine a deployment status of the associated plurality of separate wearable cardiac device components;
select the one of the operable wearable cardiac monitoring device or the operable wearable cardiac monitoring and treatment device for the patient including the plurality of the separate wearable cardiac device components on determining that the deployment status indicates that the associated plurality of separate wearable cardiac device components is ready to be deployed to the patient; and
configure the one of the operable wearable cardiac monitoring device or the operable wearable cardiac monitoring and treatment device for the patient including the associated plurality of the separate wearable cardiac device components according to the prescription for the patient.

11. The inventory management server device of claim 10, wherein the plurality of communication interface circuits comprises at least one of a Bluetooth interface circuit, a Wi-Fi interface circuit, NFC interface circuit, an RFID interface circuit, and an RFID tag.

12. The inventory management server device of claim 10, wherein the inventory information includes at least one of an identifier of the at least one component, a type of the at least one component, a quantity of the at least one component, a status of the at least one component, a location of the at least one component within a depot, and an expiration date of the at least one component.

13. The inventory management server device of claim 10, wherein the one or more prescription parameters includes one of more of an age of the patient, a gender of the patient, a size and fit of the patient, and underlying medical conditions of the patient.

14. The inventory management server device of claim 10, wherein the plurality of separate wearable cardiac device components is configured to form the operable wearable cardiac monitoring device, and wherein the memory further comprises instructions that when executed by the processor cause the processor to automatically trigger alerts for reporting information according to the one or more prescription parameters.

15. The inventory management system of claim 1, wherein the one or more prescription parameters includes one of more of an age of the patient, a gender of the patient, a size and fit of the patient, and underlying medical conditions of the patient.

16. The inventory management system of claim 1, wherein the plurality of separate wearable cardiac device components is configured to form the operable wearable cardiac monitoring device, and wherein the memory further comprises instructions that when executed by the processor cause the processor to automatically trigger alerts for reporting information according to the one or more prescription parameters.

* * * * *